(12) United States Patent
Nagamori et al.

(10) Patent No.: US 8,889,888 B2
(45) Date of Patent: Nov. 18, 2014

(54) SULFONIC ACID SALT AND DERIVATIVE THEREOF, PHOTO-ACID GENERATOR, AND PROCESS FOR PRODUCTION OF SULFONIC ACID SALT

(75) Inventors: Masashi Nagamori, Fujimino (JP); Masaki Fujiwara, Kawagoe (JP); Kazunori Mori, Iruma-gun (JP); Satoru Narizuka, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 605 days.

(21) Appl. No.: 13/000,643

(22) PCT Filed: Jul. 6, 2009

(86) PCT No.: PCT/JP2009/062278
§ 371 (c)(1),
(2), (4) Date: Dec. 22, 2010

(87) PCT Pub. No.: WO2010/007910
PCT Pub. Date: Jan. 21, 2010

(65) Prior Publication Data
US 2011/0112306 A1    May 12, 2011

(30) Foreign Application Priority Data

Jul. 14, 2008 (JP) ................. 2008-182201

(51) Int. Cl.
| | | |
|---|---|---|
| C07D 209/96 | (2006.01) |
| C07C 309/70 | (2006.01) |
| C07C 303/22 | (2006.01) |
| C07D 311/78 | (2006.01) |
| C07D 333/46 | (2006.01) |
| G03F 7/039 | (2006.01) |
| C07C 381/12 | (2006.01) |
| C07D 335/02 | (2006.01) |
| C07C 309/82 | (2006.01) |
| G03F 7/004 | (2006.01) |
| C07C 309/12 | (2006.01) |
| C07C 25/18 | (2006.01) |
| C07D 209/76 | (2006.01) |

(52) U.S. Cl.
CPC ............. *C07C 381/12* (2013.01); *C07C 303/22* (2013.01); *C07D 311/78* (2013.01); *C07D 333/46* (2013.01); *G03F 7/0397* (2013.01); *C07D 335/02* (2013.01); *C07C 309/82* (2013.01); *G03F 7/0045* (2013.01); *G03F 7/0046* (2013.01); *C07C 309/12* (2013.01); *C07C 25/18* (2013.01); *C07D 209/76* (2013.01); *C07C 2103/74* (2013.01)
USPC ............ 548/514; 548/542; 562/108; 568/842

(58) Field of Classification Search
None
See application file for complete search history.

(56) References Cited

U.S. PATENT DOCUMENTS

2010/0324329 A1* 12/2010 Nagai et al. .................. 562/108

FOREIGN PATENT DOCUMENTS

| JP | 2008-7409 A | 1/2008 |
| JP | 2008-7410 A | 1/2008 |
| KR | 10-2008-0000528 | 1/2008 |
| WO | WO 2008/056795 A1 | 5/2008 |
| WO | WO 2008/056796 A1 | 5/2008 |

OTHER PUBLICATIONS

J.V. Crivello, "Cationic Polymerization—Iodonium and Sulfanium Salt Photoinitiators", Advances in Polymer Science, 1984, p. 1-48, vol. 62.
United States Environmental Protection Agency, Perfluorooctyl Sulfonates; Proposed Significant New Use Rule, pp. 1-35, Oct. 18, 2000, vol. 65, No. 202.
International Search Report (Form PCT/ISA/210) dated Aug. 4, 2009, with English translation; including Form PCT/ISA/237 (Eight (8) pages).
Korean Office Action with Japanese translation dated Oct. 18, 2012 (nine (9) pages).

* cited by examiner

*Primary Examiner* — Michael Barker
(74) *Attorney, Agent, or Firm* — Crowell & Moring LLP

(57) ABSTRACT

A fluorine-containing sulfonic acid salt or a compound having a fluorine-containing sulfonic acid group, either of which having a structure represented by the following general formula (1), is provided. Such a salt or compound can act as a suitable photo-acid generator, and can form a resist pattern having excellent sensitivity, resolution and mask-dependence.

[Chemical Formula 99]

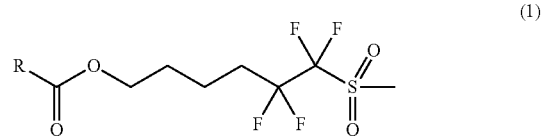

(1)

[In general formula (1), R represents a substituted or unsubstituted linear or branched monovalent hydrocarbon group having 1 to 30 carbon atoms, a substituted or unsubstituted monovalent hydrocarbon group having 3 to 30 carbon atoms and a cyclic or a partially cyclic structure, a substituted or unsubstituted aryl group having 6 to 30 carbon atoms, or a substituted or unsubstituted monovalent heterocyclic organic group having 4 to 30 carbon atoms.]

14 Claims, No Drawings

SULFONIC ACID SALT AND DERIVATIVE THEREOF, PHOTO-ACID GENERATOR, AND PROCESS FOR PRODUCTION OF SULFONIC ACID SALT

TECHNICAL FIELD

The present invention relates to a novel sulfonic acid salt and a derivative thereof, and a process for producing the sulfonic acid salt.

BACKGROUND OF THE INVENTION

In recent years, the trend toward micro-scale pattern rule has been increasing with the trend toward large-scale integration and high-speed of LSI. The trend toward a shorter wavelength of the exposure light source lies behind it. For example, it has become possible to mass-produce DRAM (dynamic random-access memory) of 64M-bit (processing dimension is 0.25 μm or less) by the wavelength shortening from mercury lamp i-line (365 nm) to KrF excimer laser (248 nm). Furthermore, in order to realize the production of DRAM's having integration degrees of 256M and 1 G or greater, a lithography using ArF excimer laser (193 nm) is getting studied seriously, in which studies on devices of 65-nm node have been made in combination with a lens of high NA (NA≥0.9). Although the use of $F_2$ laser having a wavelength of 157 nm was considered as one candidate for production of devices of 45-nm node, application thereof was postponed because of many problems represented by a more expensive scanner, change of optical system, low etching resistance and the like. Hence, the ArF immersion lithography was proposed as an alternate to $F_2$ lithography and is becoming introduced. In design rule of 45 nm or less, extreme ultraviolet ray (EUV) lithography has been hopefully expected.

As a resist suitable for such exposure wavelength, "chemically amplified resist material" attracts much attention. This contains a radiosensitive acid generator (hereinafter referred to as "photo-acid generator") which generates an acid by radiation irradiation (hereinafter, referred to as "exposure") and is a pattern-forming material that forms a pattern by making a difference in solubility in developing agent between the exposed portion and the unexposed portion through a reaction using the acid generated by the exposure as a catalyst.

By the way, photo-acid generator's characteristics desired in the chemically amplified resist material are exemplified by: an excellent transparency to radiation and excellent quantum yield at acid generation; a sufficiently high strength of acid to be generated; a sufficiently high boiling point of acid to be generated; and a moderate distance for which acid to be generated is diffused in a resist film (hereinafter referred to as "a diffusion length").

Of these, with regard to acid strength, boiling point and diffusion length, the structure of anion moiety is important in a case of an ionic radiosensitive acid generator, while that of sulfonyl moiety is important in a case of a nonionic radiosensitive acid generator having normal sulfonyl structure and sulfonic acid ester structure. For example, in a case of a radiosensitive acid generator having the trifluoromethanesulfonyl structure, the strength of acid to be generated is sufficiently high and the resolution performance for photoresist is sufficiently high; however, the mask-dependence for photoresist is increased because of a long diffusion length of acid, which is disadvantageous. Additionally, in a case of a radiosensitive acid generator having a sulfonyl structure bonded to a large organic group, such as a 10-camphorsulfonyl structure, the boiling point of acid to be generated becomes sufficiently high and the diffusion length of acid becomes sufficiently short, so that the mask-dependence is reduced; however, the acid strength is not enough, so that the resolution performance for photoresist is not sufficient.

On the other hand, a radiosensitive acid generator having perfluoroalkylsulfonyl structure, such as perfluoro-n-octanesulfonic acid (PFOS), exhibits a sufficient acidity and a substantially moderate boiling point and diffusion length of acid, so as to have received attention particularly in recent years.

If taking environmental issues into account, however, the radiosensitive acid generator having perfluoroalkylsulfonyl structure, such as perfluoro-n-octanesulfonic acid (PFOS), has low flammability in general and is suspected of accumulation in the human body. Therefore, in a report made by ENVIRONMENTAL PROTECTION AGENCY (US) (see Non-Patent Document 1), it is proposed to restrict the use thereof. In micromachining fields, it is therefore an urgent matter to develop an alternate composition which does not have such a disadvantage and is excellent in function as the radiosensitive acid generator.

REFERENCES ABOUT PRIOR ART

Non-Patent Publication

Non-Patent Publication 1: "Perfluorooctyl Sulfonates; Proposed Significant New Use Rule"

SUMMARY OF THE INVENTION

An object of the present invention is to provide: a novel acid generator relatively high in flammability, not problematic to accumulation in human body, sufficiently high in acidity and boiling point of acid to be generated, having a moderately short diffusion length in a resist film, and having a small dependence on micro-scale of a mask pattern; a novel sulfonic acid salt configuring the acid generator; a sulfonic acid derivative useful as an intermediate or raw material for synthesizing the acid generator; and a process for producing the sulfonic acid salt.

The present inventors have eagerly made studies in order to solve the above problems. As a result of this, they have achieved the finding of a fluorine-containing sulfonic acid salt or a compound having a fluorine-containing sulfonic acid group that have a structure represented by the following general formula (1).

[Chemical Formula 1]

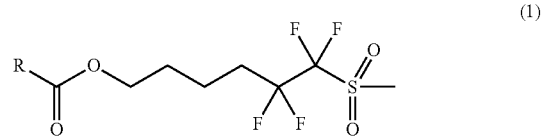

(1)

[In the general formula (1), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms.]

Of these, it has been found that a sulfonic acid represented by the following general formula (5)

[Chemical Formula 2]

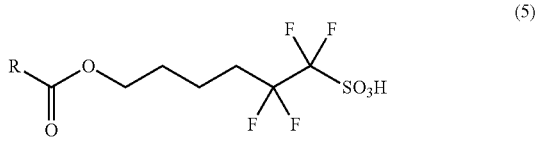

(5)

[In the general formula (5), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms.] is a sufficiently strong acid so as to be useful for formation of a resist pattern, regardless of its relatively small fluorine content (4 fluorine atoms).

Furthermore, they have found that a sulfonic acid onium salt compound represented by the following general formula (2)

[Chemical Formula 3]

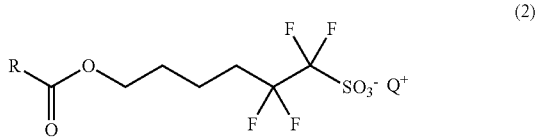

(2)

[In the general formula (2), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms. $Q^+$ represents a monovalent onion cation.] is sensitive to high energy rays such as ultraviolet rays, far ultraviolet rays, extreme ultraviolet rays (EUV), electron beam, X-rays, excimer laser, γ-rays or synchrotron radiation irradiation so as to act as a precursor compound (referred to as "a photo-acid generator") which generates a sulfonic acid represented by the general formula (5), thereby being able to form a resist pattern greatly superior to conventional ones in sensitivity, resolution and mask-dependence.

It has been found that a N-sulfonyloxyimide compound represented by the following general formula (3)

[Chemical Formula 4]

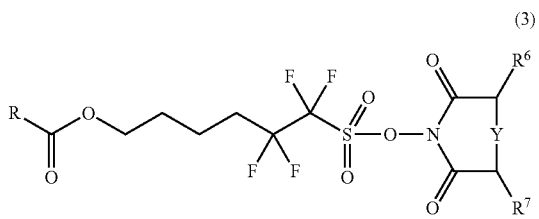

(3)

[In the general formula (3), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms. $R^6$ and $R^7$ mutually independently represent hydrogen atom or a substituted or unsubstituted monovalent organic group; alternatively, $R^6$ and $R^7$ form a ring together with the carbon atoms to which they bond mutually. Y represents a single bond, a double bond or a divalent organic group.] also is sensitive to high energy rays such as ultraviolet rays, far ultraviolet rays, extreme ultraviolet rays (EUV), electron beam, X-rays, excimer laser, γ-rays or synchrotron radiation irradiation so as to act as a photo-acid generator which generates a sulfonic acid represented by the general formula (5), thereby being able to form a resist pattern greatly superior to conventional ones in sensitivity, resolution and mask-dependence.

A fluorine-containing sulfonic acid salt or a compound having a fluorine-containing sulfonic acid group, either of which having a structure represented by the general formula (1), is typically characterized: by having has 6 carbon atoms in the parent chain; by having 4 fluorine atoms on two carbon atoms located on the side of the sulfone skeleton (a tetrafluoroethanesulfonic acid skeleton); by having an ester structure (ester skeleton) on the opposite end of the sulfone skeleton. Namely, it is deemed not only that the tetrafluoroethanesulfonic acid skeleton brings about a significant increase in acid strength but also that the ester skeleton brings about solubility in a resist solvent, compatibility with resin and control over sulfonic acid's boiling point. By the way, by arranging an ester group to be introduced, it becomes possible to adjust the boiling point or solubility of a sulfonic acid to be generated.

Furthermore, the present inventors have found a sulfonic acid salt represented by the following general formula (4)

[Chemical Formula 5]

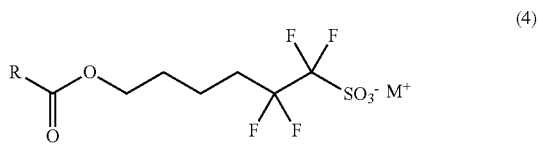

(4)

[In the general formula (4), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms. M represents Na, K or Li.] and a sulfonyl halide compound represented by the following general formula (6)

[Chemical Formula 6]

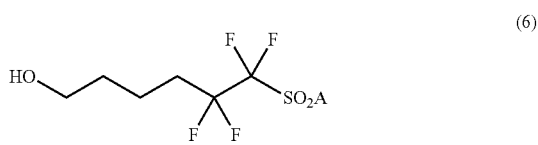

(6)

[In the general formula (6), A represents halogen atom.], which are useful as a common material for producing the above-mentioned photo-acid generator.

Additionally, in relation to these findings, each invention of a process of producing a sulfonic acid onium salt compound represented by the general formula (2) has been found, thereby achieving completion of the present invention.

More specifically, the invention of the present application involves the following [Invention 1] to [Invention 12].

[Invention 1]

A fluorine-containing sulfonic acid salt or a compound having a fluorine-containing sulfonic acid group, either of which having a structure represented by the following general formula (1).

[Chemical Formula 7]

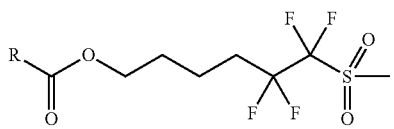
(1)

[In the general formula (1), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms.]

[Invention 2]

A sulfonic acid onium salt compound represented by the following general formula (2).

[Chemical Formula 8]

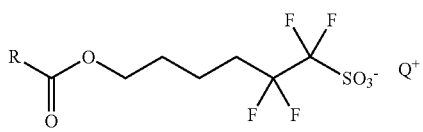
(2)

[In the general formula (2), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms. $Q^+$ represents a monovalent onion cation.]

[Invention 3]

A sulfonic acid onium salt compound as mentioned in Invention 2, wherein $Q^+$ is a sulfonium cation represented by the following general formula (i).

[Chemical Formula 9]

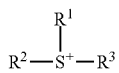
(i)

[In the general formula (1), $R^1$, $R^2$ and $R^3$ mutually independently represent a substituted or unsubstituted linear or branched alkyl group having 1 to 10 carbon atoms or a substituted or unsubstituted aryl group having 6 to 18 carbon atoms; alternatively, any two or more of $R^1$, $R^2$ and $R^3$ bond mutually to form a ring together with sulfur atom as shown in the formula.]

[Invention 4]

A sulfonic acid onium salt compound as mentioned in Invention 2, wherein $Q^+$ is an iodonium cation represented by the following general formula (ii).

[Chemical Formula 10]

$$R^4—I^+—R^5 \quad (ii)$$

[In the general formula (ii), $R^4$ and $R^5$ mutually independently represent a substituted or unsubstituted linear or branched alkyl group having 1 to 10 carbon atoms or a substituted or unsubstituted aryl group having 6 to 18 carbon atoms; alternatively, $R^4$ and $R^5$ are bonded mutually to form a ring together with iodine atom as shown in the formula.]

[Invention 5]

A N-sulfonyloxyimide compound represented by the following general formula (3).

[Chemical Formula 11]

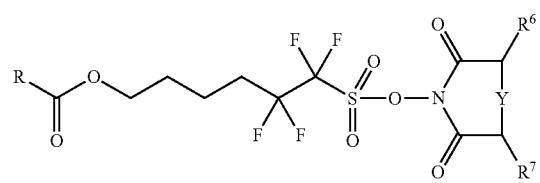
(3)

[In the general formula (3), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms. $R^6$ and $R^7$ mutually independently represent hydrogen atom or a substituted or unsubstituted monovalent organic group; alternatively, $R^6$ and $R^7$ form a ring together with the carbon atoms to which they bond mutually. Y represents a single bond, a double bond or a divalent organic group.]

[Invention 6]

A sulfonic acid salt represented by the following general formula (4).

[Chemical Formula 12]

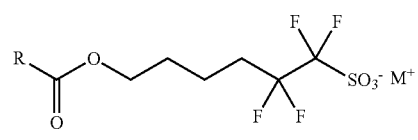
(4)

[In the general formula (4), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms. M represents Na, K or Li.]

[Invention 7]

A sulfonic acid represented by the following general formula (5).

[Chemical Formula 13]

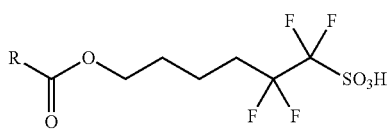

[In the general formula (5), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms.]

[Invention 8]

A sulfonyl halide compound represented by the following general formula (6).

[Chemical Formula 14]

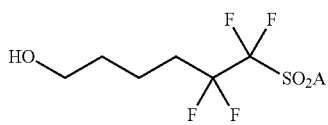

[In the general formula (6), A represents halogen atom.]

[Invention 9]

A radiosensitive acid generator for a chemically amplified resist material, characterized by being sensitive to high energy rays such as ultraviolet rays, far ultraviolet rays, extreme ultraviolet rays (EUV), electron beam, X-rays, excimer laser, γ-rays or synchrotron radiation irradiation, thereby generating a sulfonic acid as mentioned in Invention 7.

[Invention 10]

A radiosensitive acid generator for a chemically amplified resist material, characterized by being sensitive to high energy rays such as ultraviolet rays, far ultraviolet rays, extreme ultraviolet rays (EUV), electron beam, X-rays, excimer laser, γ-rays or synchrotron radiation irradiation and by containing a sulfonic acid onium salt compound as mentioned in any of Invention 2 to Invention 4 or a N-sulfonyloxyimide compound as mentioned in Invention 5.

[Invention 11]

Triphenylsulfonium 1,1,2,2-tetrafluoro-6-(1-adamantanecarbonyloxy)-hexane-1-sulfonate

[Invention 12]

A process for producing a sulfonic acid onium salt compound represented by the following general formula (2)

[Chemical Formula 15]

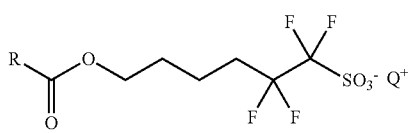

comprising the following 4 steps.

A $1^{st}$ step: A step of sulfinating 6-bromo-5,5,6,6-tetrafluorohexan-1-ol by using a sulfinating agent thereby obtaining a sulfinic acid salt represented by the following general formula (7).

[Chemical Formula 16]

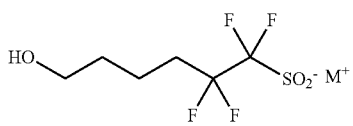

A $2^{nd}$ step: A step of oxidizing the sulfinic acid salt obtained by the $1^{st}$ step and represented by the general formula (7) by using an oxidizing agent, thereby obtaining a sulfonic acid salt represented by the following general formula (4).

[Chemical Formula 17]

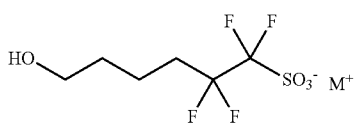

A $3^{rd}$ step: A step of reacting the sulfonic acid salt obtained by the $2^{nd}$ step and represented by the general formula (4) with a monovalent onium salt represented by the following general formula (8)

[Chemical Formula 18]

$$Q^+X^- \quad (8)$$

thereby obtaining a sulfonic acid onium salt represented by the following general formula (9).

[Chemical Formula 19]

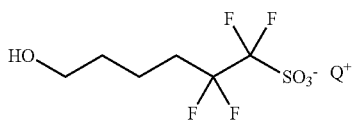

A $4^{th}$ step: A step of reacting the sulfonic acid onium salt obtained by the $3^{rd}$ step and represented by the general formula (9) with acid or acid halide represented by the following general formula (10)

[Chemical Formula 20]

or with acid anhydride represented by the following general formula (11)

[Chemical Formula 21]

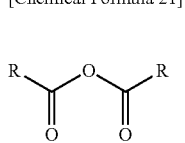

thereby obtaining a sulfonic acid onium salt compound represented by the general formula (2).

[In the general formula (2), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms. $Q^+$ represents a monovalent onium cation. In the general formula (7) and the general formula (4), M represents Na, K or Li. In the general formula (8), $Q^+$ has the same meaning as that of $Q^+$ in the general formula (2), while $X^-$ represents a monovalent anion. In the general formula (9), $Q^+$ has the same meaning as that of $Q^+$ in the general formula (2). In the general formula (10), $X^-$ represents hydroxyl group, fluorine atom, chlorine atom, bromine atom or iodine atom, while R has the same meaning as that of R in the general formula (2). R in the general formula (11) has the same meaning as that of R in the general formula (2).]

DETAILED DESCRIPTION

A fluorine-containing sulfonic acid salt or a compound having a fluorine-containing sulfonic acid group, according to the present invention has in its structure a small proportion of fluorine atom so as to be small in concern about biological concentration and accumulation; however, the acidity thereof stemmed from acids generated by exposure is sufficiently high. Moreover, the structure of the photo-generated acid can be readily adjusted; as a result, the photo-generated acid can be prevented from diffusion and controlled in boiling point, thereby avoiding such a problem that the photo-generated acid is volatilized or eluted to water.

In the case of forming a resist material by using a fluorine-containing sulfonic acid onium salt of the present invention as a photo-acid generator, the material is to be sensitive to high energy rays such as ultraviolet rays, far ultraviolet rays, extreme ultraviolet rays (EUV), electron beam, X-rays, excimer laser, γ-rays, synchrotron radiation irradiation or the like and therefore to be act thereon as the photo-acid generator, thereby enabling the formation of a resist pattern superior to conventional ones in sensitivity, resolution and mask-dependence.

The present invention provides beneficial effects as discussed above.

Hereinafter, embodiments of the present invention will be discussed; however, the present invention is not limited to these embodiments. It should be understood that those obtained by adding suitable changes, modifications and the like to the following embodiments, based on a normal knowledge of a person skilled in the art, are included in the scope of the present invention, to the extent of not diverging from the gist of the present invention. Incidentally, omission marks discussed in the examples are as follows.

First of all, relationships among substances relating to the present invention will be shown by the following Scheme 1 and Scheme 2.

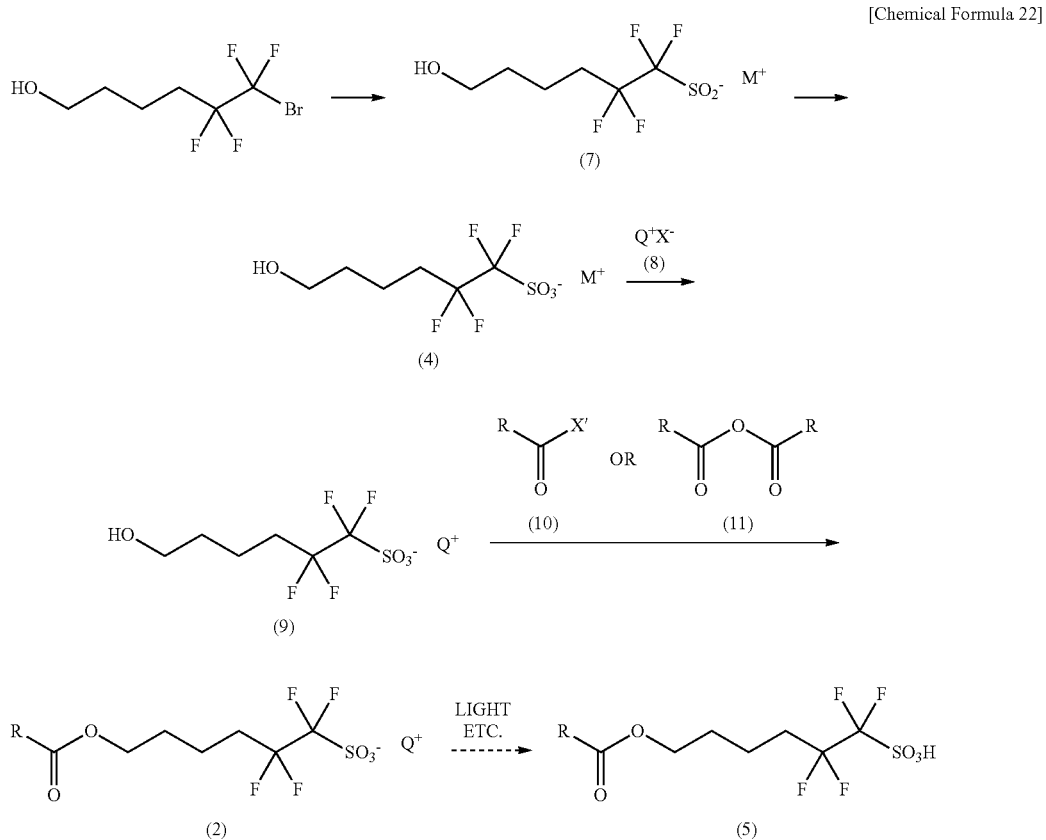

SCHEME 1

[Chemical Formula 22]

[In Scheme 1, M represents Na, K or Li. $Q^+$ represents a monovalent onion cation while $X^-$ represents a monovalent anion. R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms. X' represents hydroxyl group, fluorine atom, chlorine atom, bromine atom or iodine atom.]

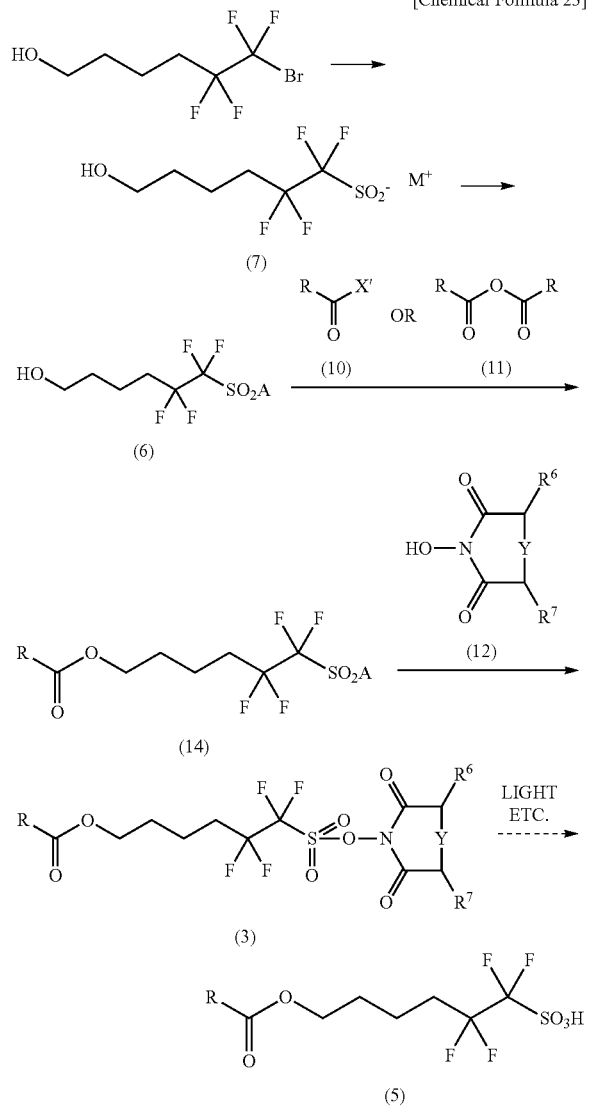

SCHEME 2

[Chemical Formula 23]

[In Scheme 2, M represents Na, K or Li. R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms. X' represents hydroxyl group, fluorine atom, chlorine atom, bromine atom or iodine atom. A represents halogen atom. $R^6$ and $R^7$ mutually independently represent hydrogen atom or a substituted or unsubstituted monovalent organic group; alternatively, $R^6$ and $R^7$ form a ring together with the carbon atoms to which they bond mutually. Y represents a single bond, a double bond or a divalent organic group.]

As shown in Scheme 1 and Scheme 2, either of the fluorine-containing sulfonic acid salt and the compound having a fluorine-containing sulfonic acid group, according to the present invention and having a structure represented by the following general formula (1)

[Chemical Formula 24]

can be introduced from 6-bromo-5,5,6,6-tetrafluorohexan-1-ol.

[In the general formula (1), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms.]

[Fluorine-Containing Sulfonic Acid Salt or Compound Having a Fluorine-Containing Sulfonic Acid Group]

First of all, a fluorine-containing sulfonic acid salt or a compound having a fluorine-containing sulfonic acid group, according to the present invention and having a structure represented by the general formula (1) will be discussed.

In the general formula (1), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms.

Hereinafter, R will be more concretely discussed. Examples of a unsubstituted linear or branched monovalent hydrocarbon group having 1 to 30 carbon atoms include methyl group, ethyl group, n-propyl group, i-propyl group, n-butyl group, t-butyl group, n-pentyl group, i-pentyl group, n-hexyl group, i-hexyl group, n-heptyl group, n-octyl group, i-octyl group, n-nonyl group, n-decyl group, 2-ethylhexyl group and n-dodecyl group.

Additionally, examples of substituents for the hydrocarbon group includes: halogen such as fluorine, chlorine, bromine and iodine; hydroxyl group; thiol group; aryl group; alkenyl group; and an organic group containing heteroatom such as halogen atom, oxygen atom, nitrogen atom, sulfur atom, phosphorous atom and silicon atom. Examples of the substituents may further include a keto group in which two hydrogen atoms on the same carbon in the hydrocarbon group are substituted with one oxygen atom. The existing number of these substituents is not limited within the scope structurally possible.

The linear or branched monovalent hydrocarbon group having 1 to 30 carbon atoms, which is substituted with the above substituents, may be exemplified by benzyl group, methoxymethyl group, methylthiomethyl group, ethoxymethyl group, phenoxymethyl group, methoxycarbonylmethyl group, ethoxycarbonylmethyl group, acetylmethyl group, fluoromethyl group, trifluoromethyl group, 2,2,2-trifluoroethyl group, chloromethyl group, trichloromethyl group, 2-fluoropropyl group, trifluoroacetylmethyl group, trichloroacetylmethyl group, pentafluorobenzoylmethyl group, aminomethyl group, cyclohexylaminomethyl group, diphenylphosphinomethyl group, trimethylsilylmethyl group, 2-phenylethyl group, 3-phenylpropyl group, 2-aminoethyl group, hydroxymethyl group, hydroxyethyl group, hydroxycarbonylmethyl group, etc.

Examples of a monovalent hydrocarbon group having a cyclic or a partially cyclic structure and having 3 to 30 carbon atoms include cyclopropyl group, cyclobutyl group, cyclopentyl group, cyclohexyl group, bornyl group, norbornyl group, adamantyl group, pinanyl group, thujyl group, caryl group, camphanyl group, cyclopropylmethyl group, cyclobutylmethyl group, cyclopentylmethyl group, cyclohexylmethyl group, bornylmethyl group, norbornylmethyl group and adamantylmethyl group.

Additionally, examples of substituents for the hydrocarbon group includes: halogen such as fluorine, chlorine, bromine and iodine; hydroxyl group; thiol group; aryl group; alkenyl group; and an organic group containing heteroatom such as halogen atom, oxygen atom, nitrogen atom, sulfur atom, phosphorous atom and silicon atom. Examples of the substituents may further include a keto group in which two hydrogen atoms on the same carbon in the hydrocarbon group are substituted with one oxygen atom. The existing number of these substituents is not limited within the scope structurally possible.

Examples of a monovalent hydrocarbon group having a cyclic or a partially cyclic structure, having 3 to 30 carbon atoms and substituted with the above substituents include 4-fluorocyclohexyl group, 4-hydroxycyclohexyl group, 4-methoxycyclohexyl group, 4-methoxycarbonylcyclohexyl group, 3-methoxycarbonyl-1-adamantyl group, 3-hydroxycarbonyl-1-adamantyl group and 3-hydroxymethyl-adamantanemethyl group.

Examples of aryl group having 6 to 30 carbon atoms are phenyl group, 1-naphthyl group, 2-naphthyl group, anthryl group, phenanthryl group. Examples of substituents for the aryl group include: halogen such as fluorine, chlorine, bromine and iodine; hydroxyl group; thiol group; aryl group; alkenyl group; and an organic group containing heteroatom such as halogen atom, oxygen atom, nitrogen atom, sulfur atom, phosphorous atom and silicon atom. Examples of a substituted aryl group having 6 to 30 carbon atoms include o-hydroxyphenyl group, m-hydroxyphenyl group, p-hydroxyphenyl group, 3,5-bis(hydroxy)phenyl group, o-tolyl group, m-tolyl group, p-tolyl group, p-methoxyphenyl group, mesityl group, o-cumenyl group, 2,3-xylyl group, o-fluorophenyl group, m-fluorophenyl group, p-fluorophenyl group, o-trifluoromethylphenyl group, m-trifluoromethylphenyl group, p-trifluoromethylphenyl group, 3,5-bis(trifluoromethyl)phenyl group, p-bromophenyl group, p-chlorophenyl group and p-iodophenyl group.

Examples of a monovalent heterocyclic organic group having 4 to 30 carbon atoms are furyl group, thienyl group, piranyl group, pyrrolyl group, thianthrenyl group, pyrazolyl group, isothiazolyl group, isoxazolyl group, pyrazinyl group, pyrimidinyl group, pyradazinyl group and monocyclic or polycyclic lactone. Of these, the monocyclic or polycyclic lactone is exemplified by γ-butyrolactone, γ-valerolactone, angelica lactone, γ-hexylactone, γ-heptalactone, γ-octalactone, γ-nonalactone, 3-methyl-4-octanolyde (whisky lactone), γ-decalactone, γ-undecalactone, γ-dodecalactone, γ-jasmolactone (7-decenolactone), δ-hexylactone, 4,6,6(4,4,6)-trimethyltetrahydropyran-2-one, δ-octalactone, δ-nonalactone, δ-decalactone, δ-2-decenolactone, δ-undecalactone, δ-dodecalactone, δ-tridecalactone, δ-tetradecalactone, lactoscaton, ε-decalactone, ε-dodecalactone, cyclohexyllactone, jasmine lactone, cis-jasmone lactone, methyl γ-decalactone, and the followings.

[Chemical Formula 25]

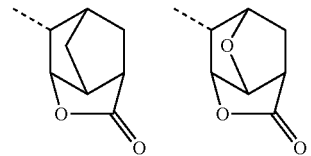

Additionally, examples of substituents for the heterocyclic organic group includes: halogen such as fluorine, chlorine, bromine and iodine; hydroxyl group; thiol group; aryl group; alkenyl group; and an organic group containing heteroatom such as halogen atom, oxygen atom, nitrogen atom, sulfur atom, phosphorous atom and silicon atom. Examples of the substituents may further include a keto group in which two hydrogen atoms on the same carbon in the heterocyclic organic group are substituted with one oxygen atom. The existing number of these substituents is not limited within the scope structurally possible.

Examples of a substituted monovalent heterocyclic organic group having 4 to 30 are 2-bromofuryl group and 3-methoxythienyl group.

Accordingly, the structure represented by the general formula (1) can be exemplified more concretely as follows.

[Chemical Formula 26]

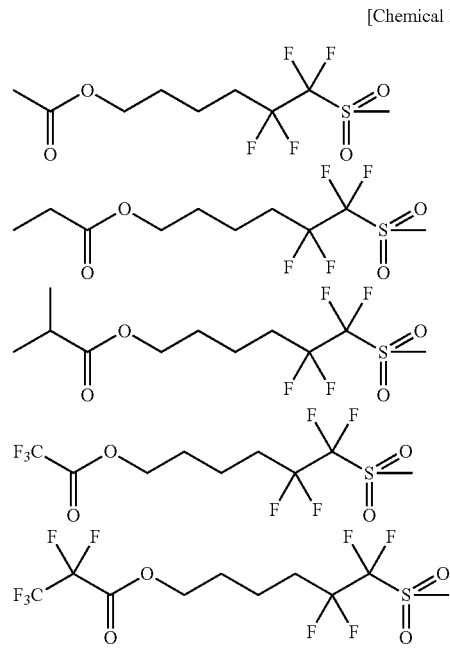

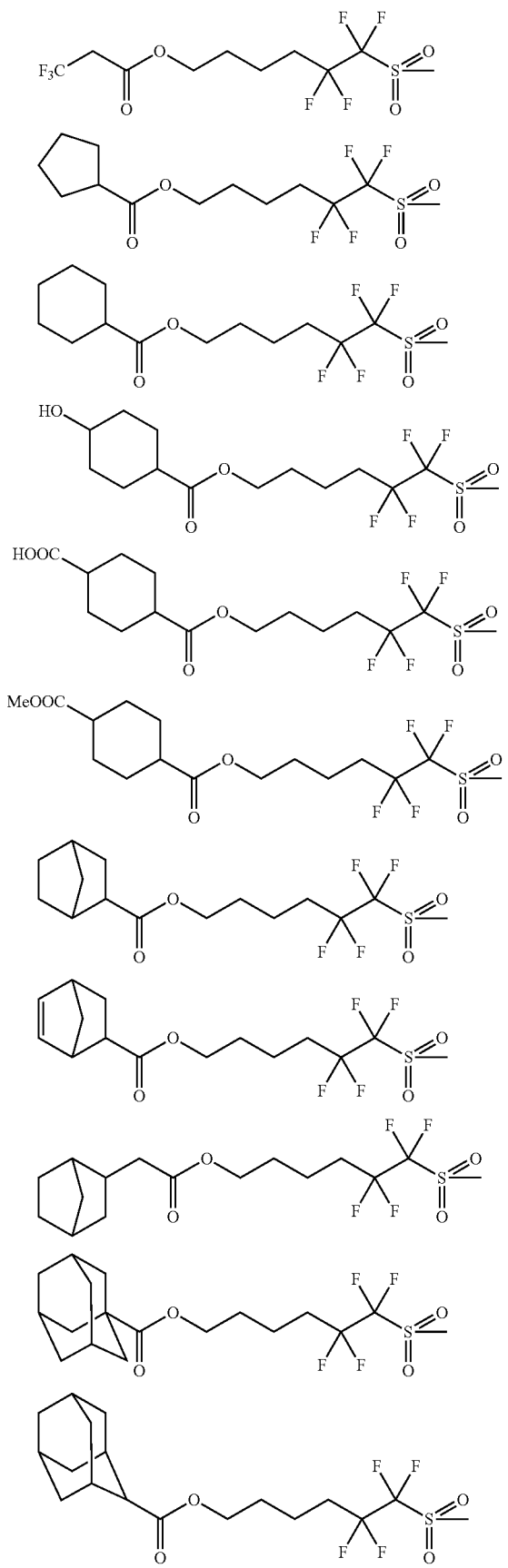
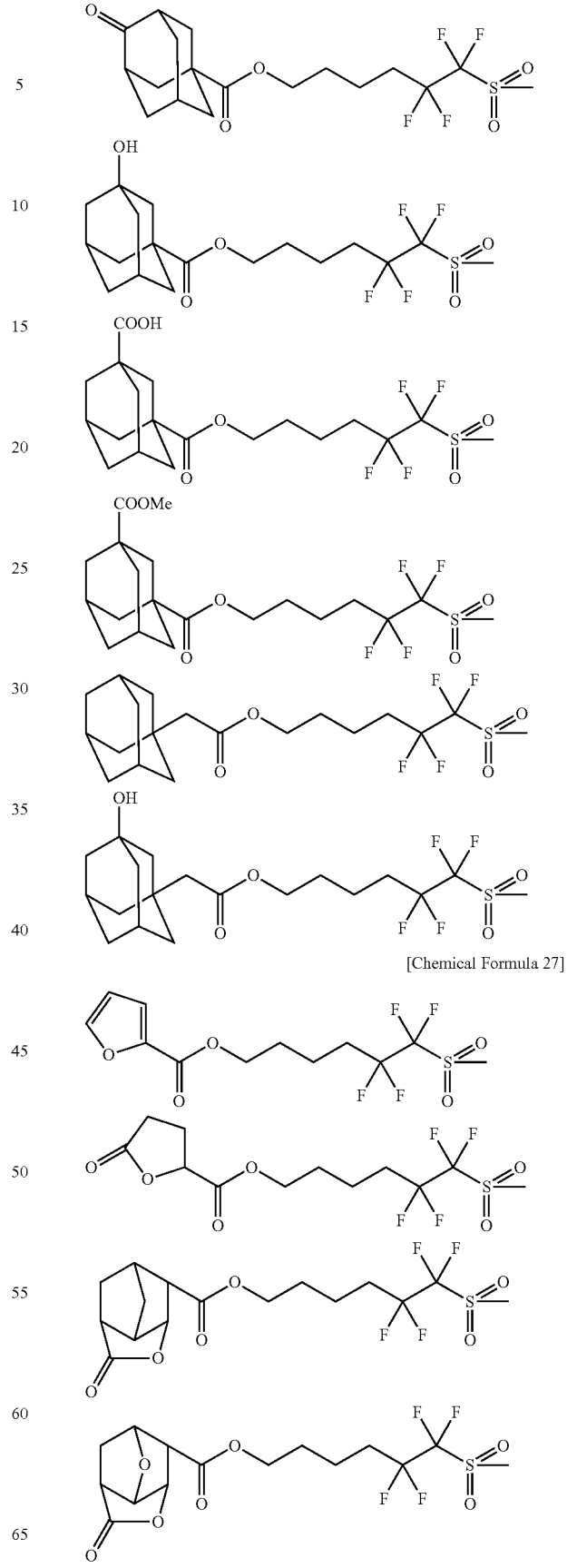

-continued

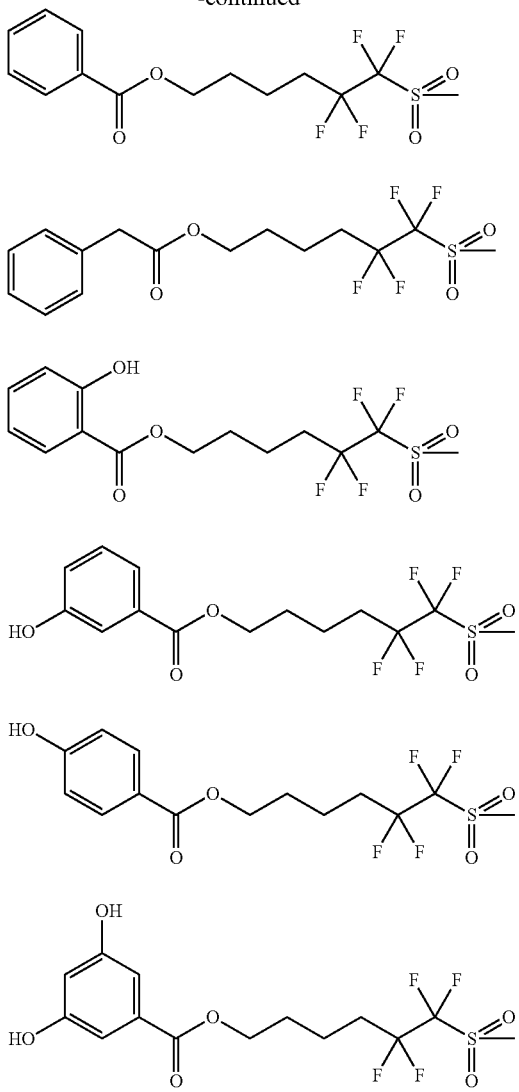

[Photo-Acid Generator]

A photo-acid generator for the present invention is sensitive to high energy rays such as ultraviolet rays, far ultraviolet rays, extreme ultraviolet rays (EUV), electron beam, X-rays, excimer laser, γ-rays or synchrotron radiation irradiation so as to generate sulfonic acid represented by the following general formula (5), which is used as a photo-acid generator for a chemically amplified resist material.

[Chemical Formula 28]

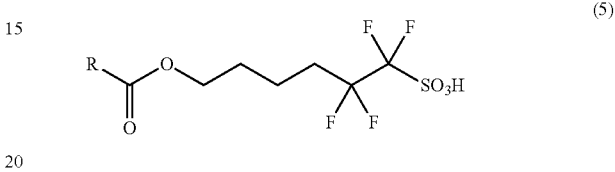

(5)

[In the general formula (5), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms.]

The concrete structure of R in the general formula (5) is exemplified again by the concrete structure as exemplified by the general formula (1).

Sulfonic acid of the present invention, which is represented by the above general formula (5), can be formed by irradiating a sulfonic acid onium salt compound represented by the general formula (2) or a N-sulfonyloxyimide compound represented by the general formula (3) with high energy rays such as ultraviolet rays, far ultraviolet rays, extreme ultraviolet rays (EUV), electron beam, X-rays, excimer laser, γ-rays or synchrotron radiation irradiation (Scheme 3).

SCHEME 3

[Chemical Formula 29]

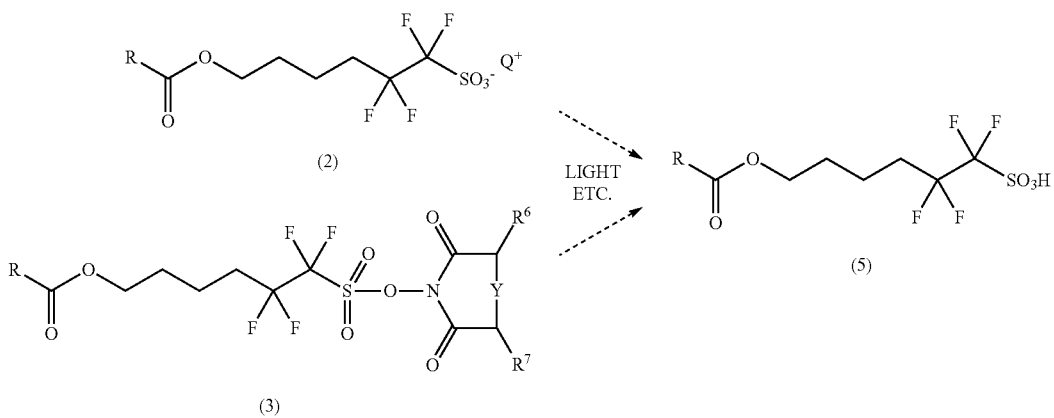

[In the general formula (2) as shown in Scheme 3, R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms. $Q^+$ represents a monovalent onion cation. In the general formula (3), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms. $R^6$ and $R^7$ mutually independently represent hydrogen atom or a substituted or unsubstituted monovalent organic group; alternatively, $R^6$ and $R^7$ form a ring together with the carbon atoms to which they bond mutually. Y represents a single bond, a double bond or a divalent organic group.]

Accordingly, a sulfonic acid onium salt compound represented by the general formula (2) and a N-sulfonyloxyimide compound represented by the general formula (3) can be used as the photo-acid generator.

The photo-acid generator of the present invention contains a sulfonic acid onium salt compound represented by the general formula (2) or a N-sulfonyloxyimide compound represented by the general formula (3) as the active component. By mixing the photo-acid generator of the present invention with a resin (a photosensitive resin) that changes solubility in alkali developing solution by an action of acid, a usable photosensitive resin composition (resist material) can be formed.

[Sulfonic Acid Onium Salt Compound]

A sulfonic acid onium salt compound, which is one photo-acid generator according to the present invention, is represented by the following general formula (2).

[Chemical Formula 30]

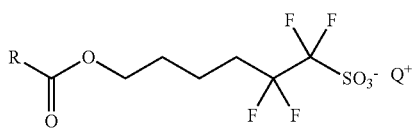

(2)

[In the general formula (2), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms. $Q^+$ represents a monovalent onion cation.]

The concrete structure of R in the general formula (2) is exemplified again by the concrete structure as exemplified by the general formula (1).

Examples of monovalent onion cation represented by $Q^+$ as shown in the general formula (2) include onium cations such as O, S, Se, N, P, As, Sb, Cl, Br and I. Among these onium cations, onium cation of S or I is preferable.

Examples of a monovalent onion cation represented by $Q^+$ as shown in the general formula (2) are those represented by the following general formula (1) or the general formula (ii).

[Chemical Formula 31]

(i)

[In the general formula (i), $R^1$, $R^2$ and $R^3$ mutually independently represent a substituted or unsubstituted linear or branched alkyl group having 1 to 10 carbon atoms or a substituted or unsubstituted aryl group having 6 to 18 carbon atoms; alternatively, any two or more of $R^1$, $R^2$ and $R^3$ bond mutually to form a ring together with the sulfur atom as shown in the formula.]

[Chemical Formula 32]

(ii)

[In the general formula (ii), $R^4$ and $R^5$ mutually independently represent a substituted or unsubstituted linear or branched alkyl group having 1 to 20 carbon atoms or a substituted or unsubstituted aryl group having 6 to 20 carbon atoms; alternatively, $R^4$ and $R^5$ are bonded mutually to form a ring together with the iodine atom as shown in the formula.]

An onium cation portion of a monovalent onium cation represented by $Q^+$ can be produced according to the common method disclosed by "J. V. Crivello, Advances in Polymer Science 62, 1, 1984", for example.

[Chemical Formula 33]

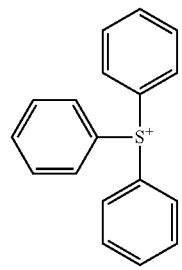

(i-1)

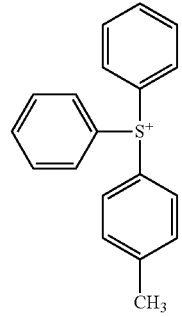

(i-2)

(i-3)
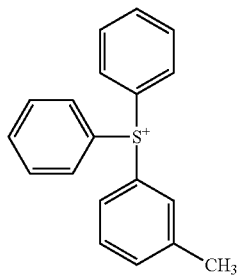
(i-4)
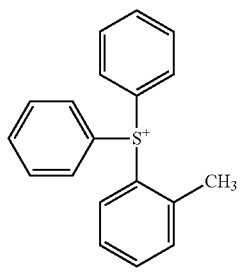
(i-5)
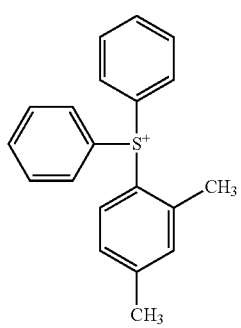
(i-6)
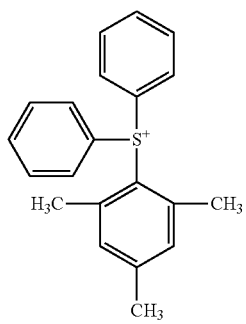
(i-7)
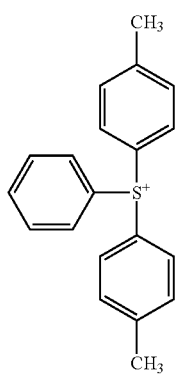
(i-8)
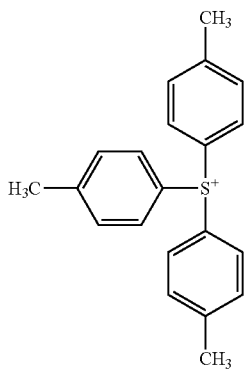
(i-9)
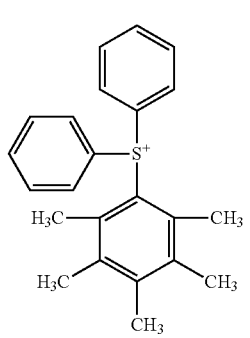
(i-10)
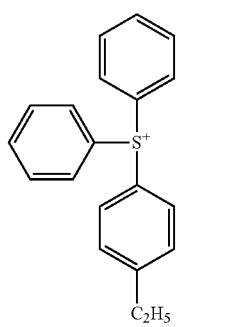
(i-11)
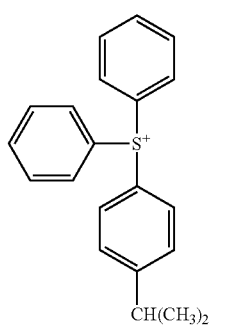

(i-12) 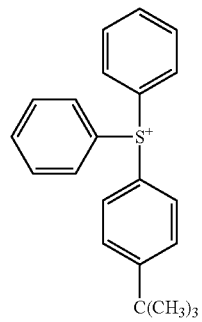
(i-13) 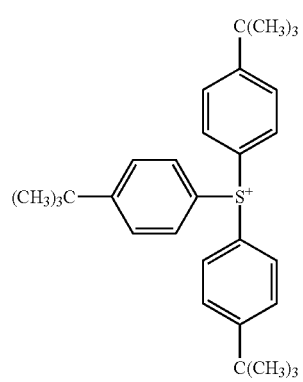
(i-14) 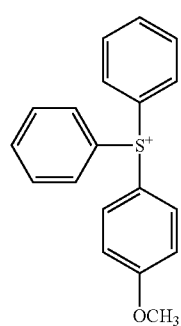
(i-15) 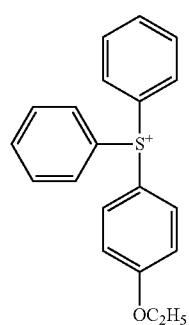
(i-16) 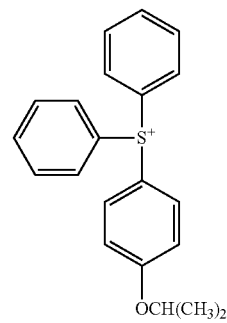
(i-17) 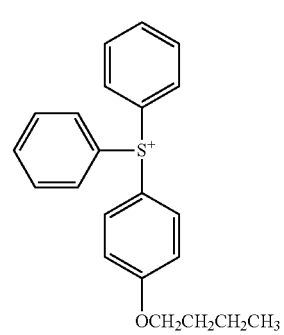
(i-18) 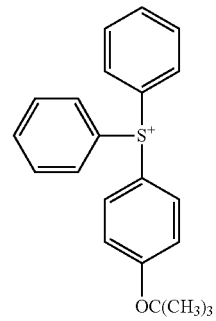
(i-19) 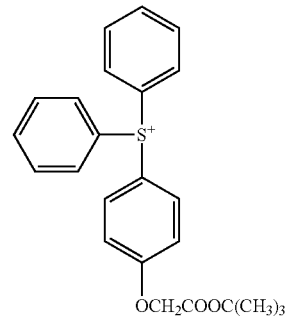

(i-20)
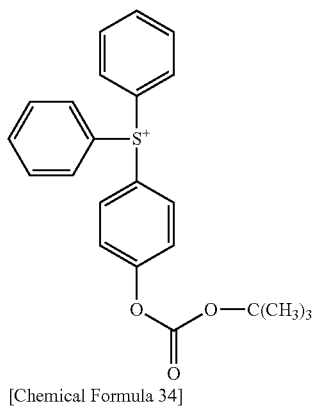
[Chemical Formula 34]
(i-21)
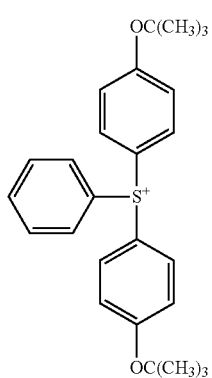
(i-22)
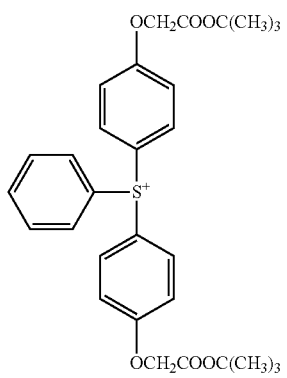
(i-23)
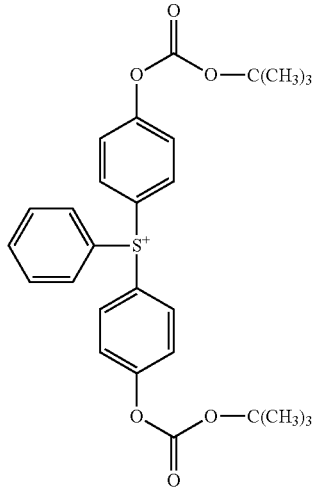
(i-24)
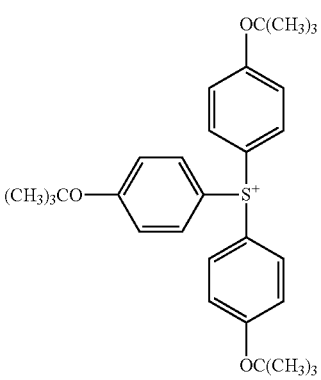
(i-25)
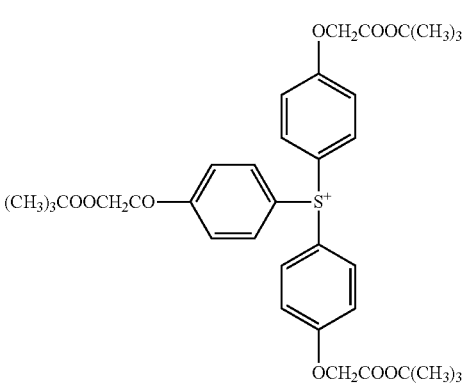
(i-26)
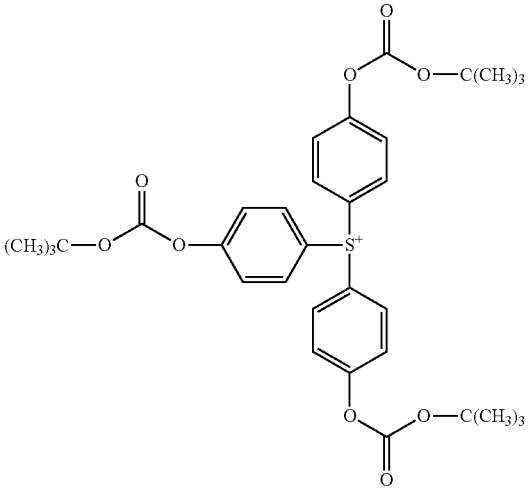
(i-27)
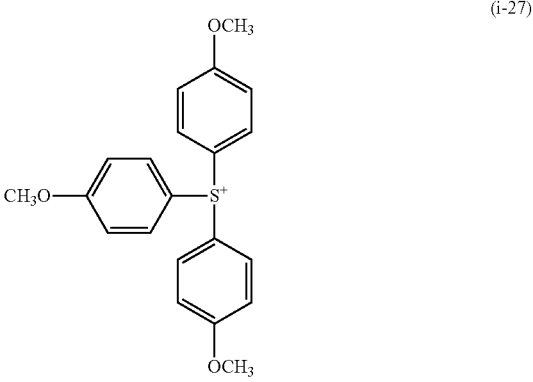

(i-28)
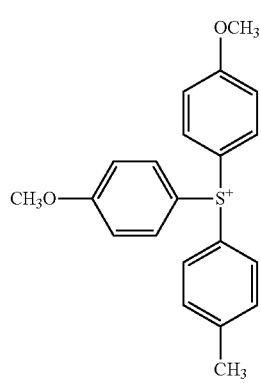
(i-29)
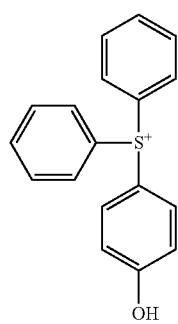
(i-30)
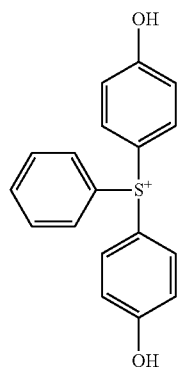
(i-31)
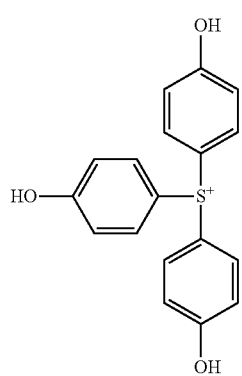
(i-32)
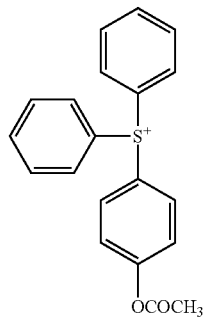
(i-33)
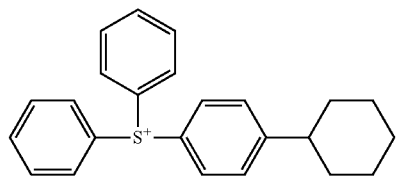
[Chemical Formula 35]
(i-34)
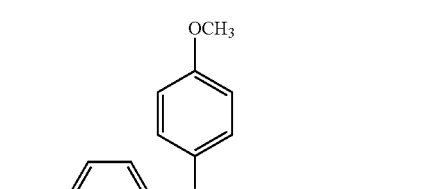
(i-35)
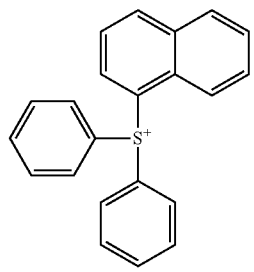
(i-36)
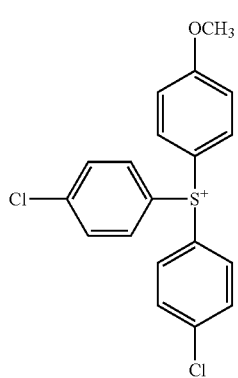
(i-37)
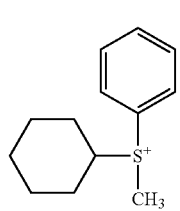

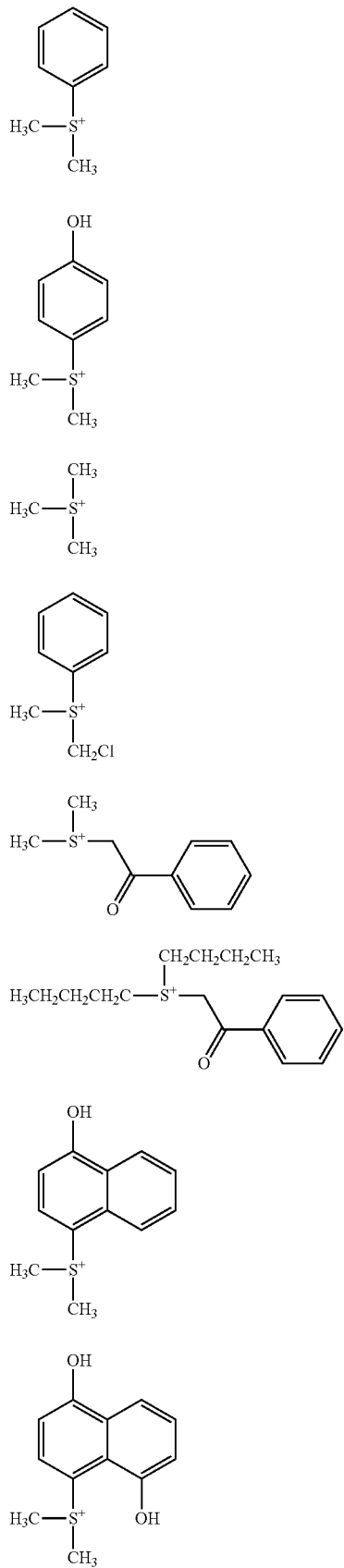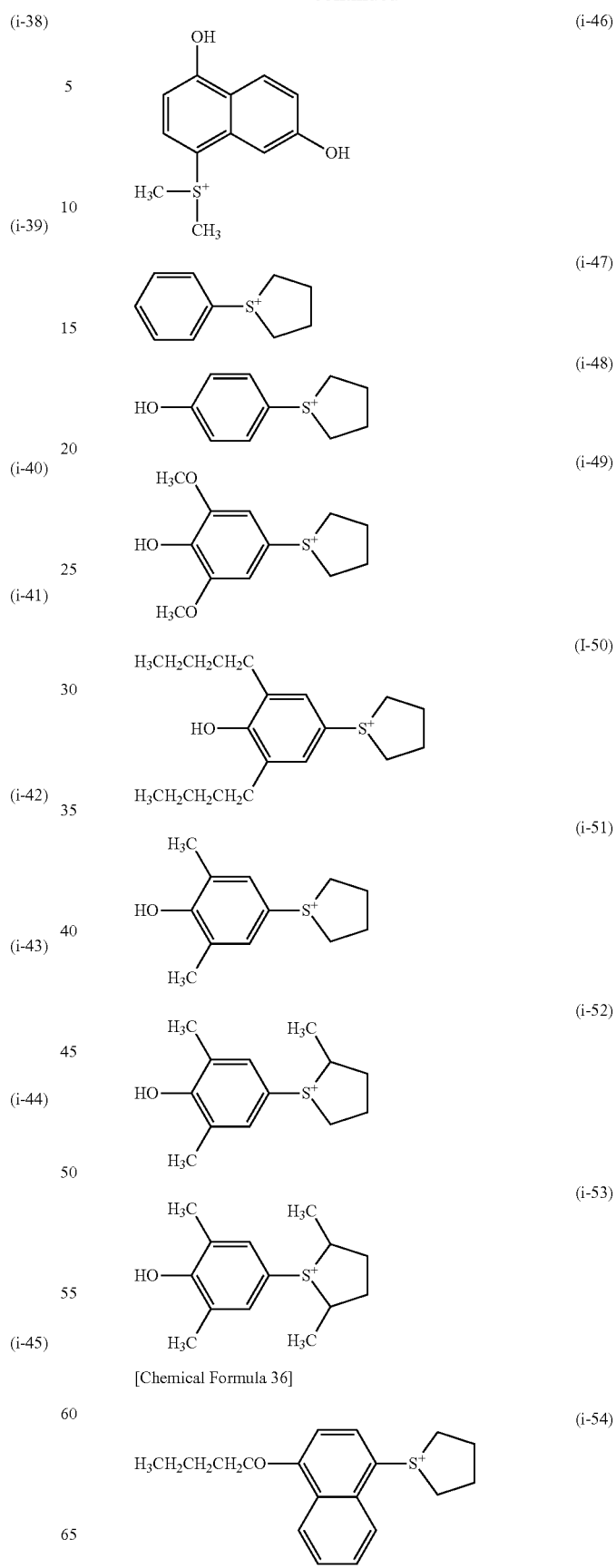
[Chemical Formula 36]

(i-55) 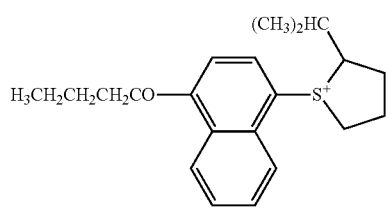
(i-56) 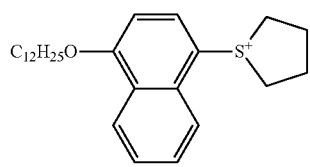
(i-57) 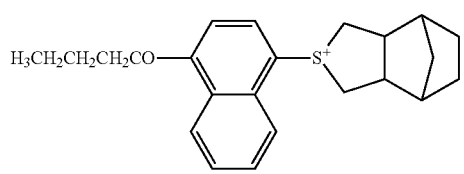
(i-58) 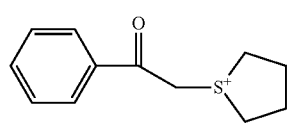
(i-59) 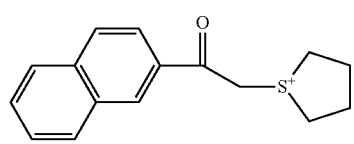
(i-60) 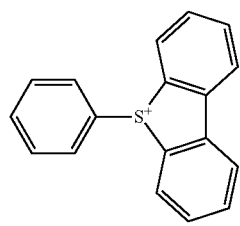
(i-61) 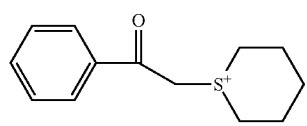
(i-62) 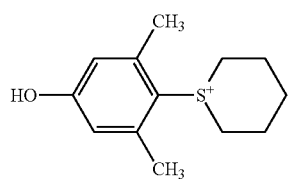
(i-63) 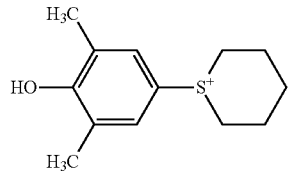
(i-64) 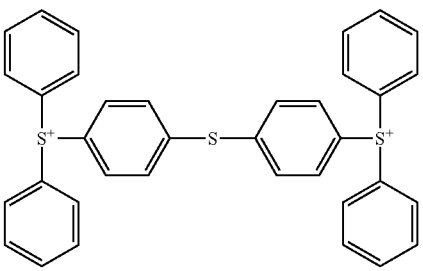
[Chemical Formula 37]
(ii-1) 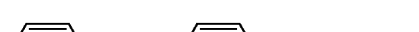
(ii-2) 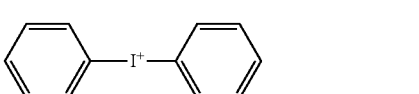
(ii-3) 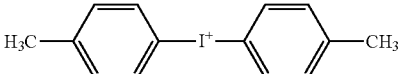
(ii-4) 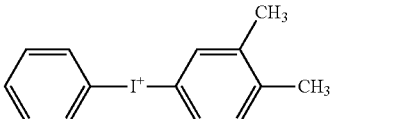
(ii-5) 
(ii-6) 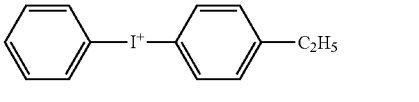
(ii-7) 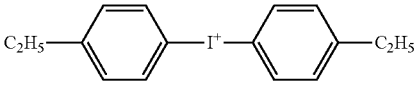
(ii-8) 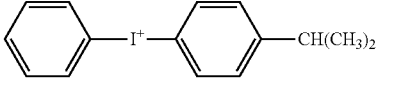
(ii-9) 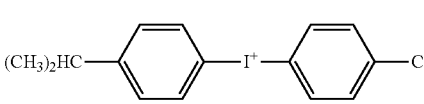
(ii-10) 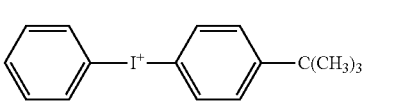
(ii-11) 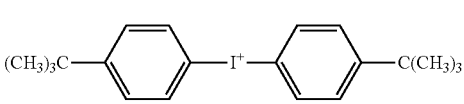
(ii-12)

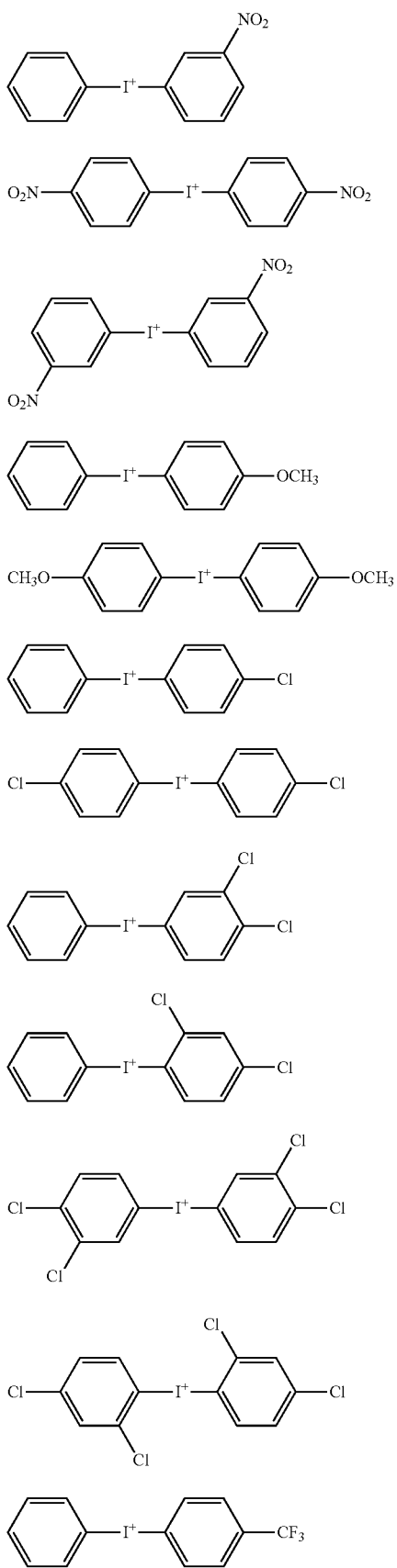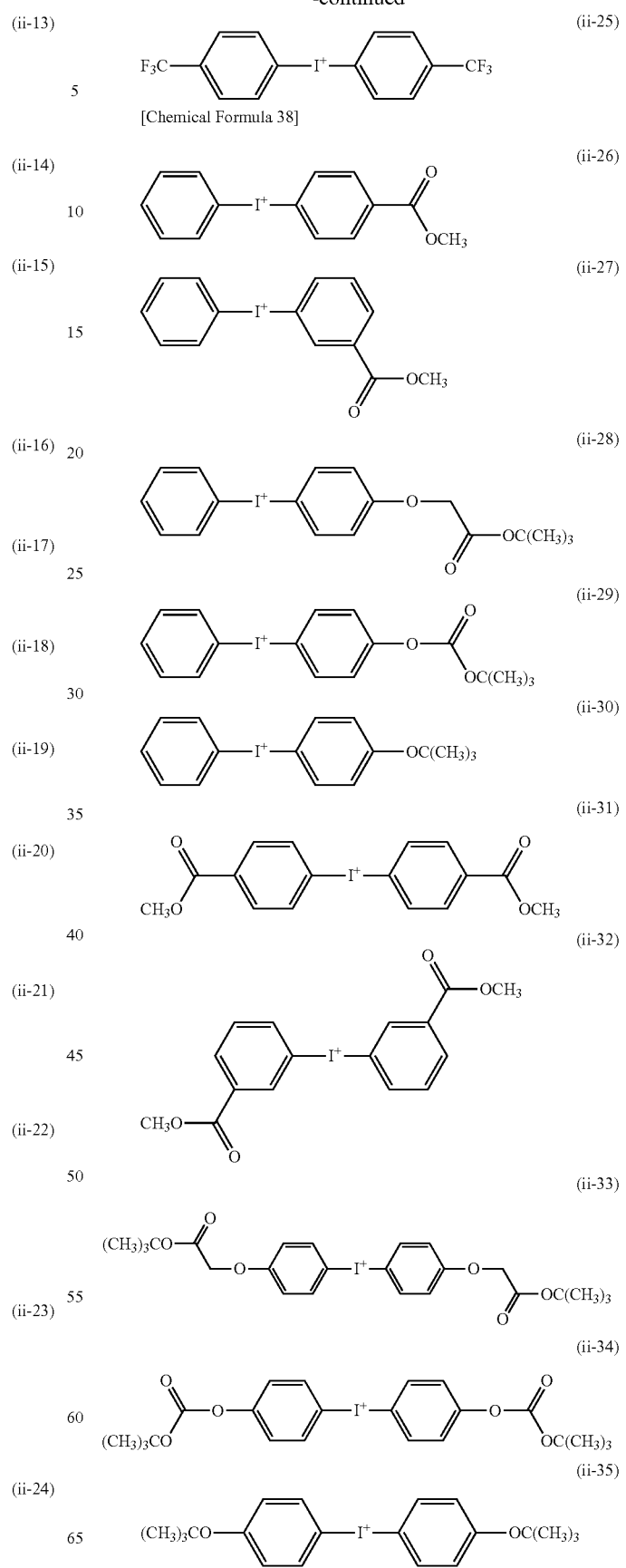

(ii-36)
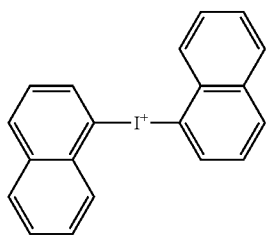

(ii-37)
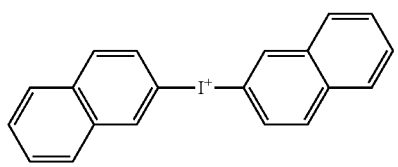

(ii-38)
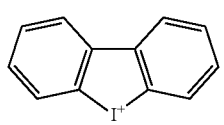

(ii-39)
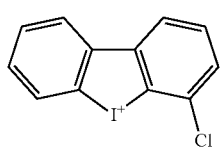

Among these monovalent onium cations, preferable examples are: sulfonium cation represented by the above formula (i-1), the formula (i-2), the formula (i-6), the formula (i-8), the formula (i-13), the formula (i-19), the formula (i-25), the formula (i-27), the formula (i-29), the formula (i-51) or the formula (i-54); iodonium cation represented by the above formula (ii-1) or the formula (ii-11); and the like.

Additionally, a preferable sulfonic acid onium salt compound comprising a combination of a preferable anion and a preferable monovalent onium cation can be exemplified by the following compounds.

(a) Triphenylsulfonium 1,1,2,2-Tetrafluoro-6-(1-Adamantanecarbonyloxy)Hexane-1-Sulfonate

[Chemical Formula 39]

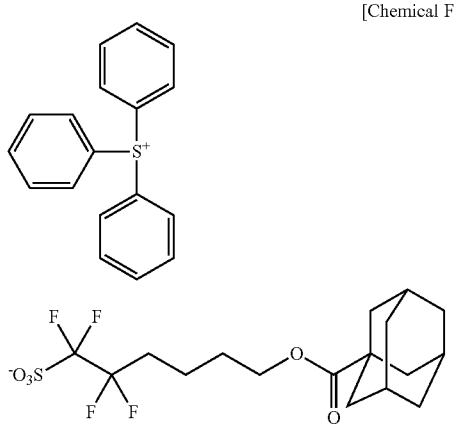

(b) Diphenyliodonium 1,1,2,2-Tetrafluoro-6-(1-Adamantanecarbonyloxy)Hexane-1-Sulfonate

[Chemical Formula 40]

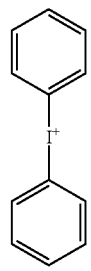

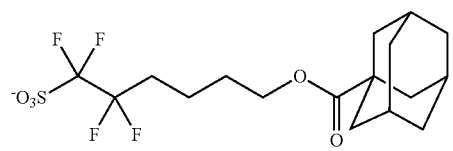

(c) Triphenylsulfonium 1,1,2,2-Tetrafluoro-6-Acetoxyhexane-1-Sulfonate

[Chemical Formula 41]

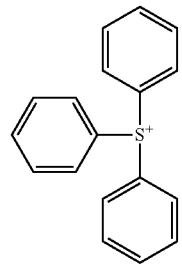

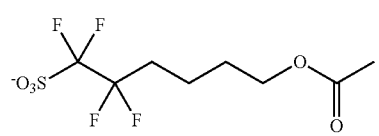

(d) Triphenylsulfonium 1,1,2,2-Tetrafluoro-6-(o-hydroxybenzoyloxy)-1-Sulfonate

[Chemical Formula 42]

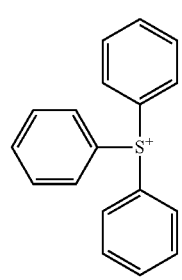

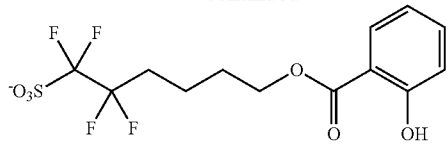

(e) Triphenylsulfonium 1,1,2,2-Tetrafluoro-6-(p-hydroxybenzoyloxy)-1-Sulfonate

[Chemical Formula 43]

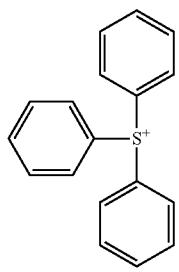

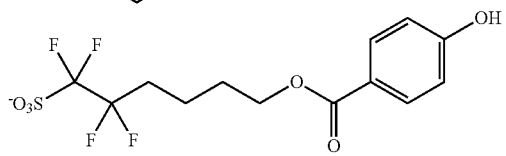

A process for producing a sulfonic acid onium salt compound represented by the general formula (2) will be discussed later.

[N-Sulfonyloxyimide Compound]

A N-sulfonyloxyimide compound, which is one of the photo-acid generator of the present invention, is represented by the general formula (3).

[Chemical Formula 44]

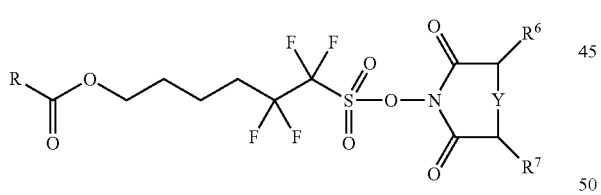

(3)

[In the general formula (3), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms. $R^6$ and $R^7$ mutually independently represent hydrogen atom or a substituted or unsubstituted monovalent organic group; alternatively, $R^6$ and $R^7$ form a ring together with the carbon atoms to which they bond mutually. Y represents a single bond, a double bond or a divalent organic group.]

The concrete structure of R in the general formula (3) is exemplified again by the concrete structure as exemplified by the general formula (1).

In the general formula (3), preferable examples of imide groups each of which is bonded to sulfonyloxy group in each formula include groups represented by the following formulas (iii-1) to (iii-9).

[Chemical Formula 45]

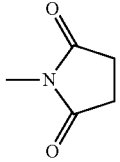 (iii-1)

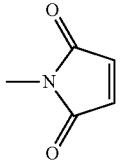 (iii-2)

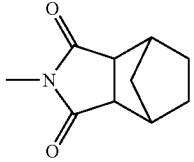 (iii-3)

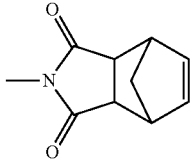 (iii-4)

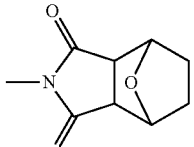 ((iii-5)

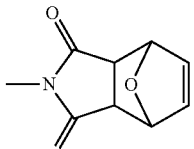 (iii-6)

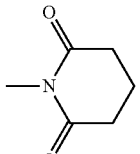 (iii-7)

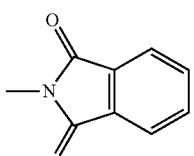 (iii-8)

-continued

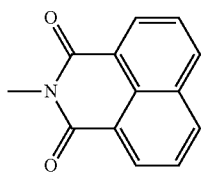
(iii-9)

Among these imide groups, the preferable group is group represented by the above formulas (iii-a), the formula (iii-4), the formula (iii-8), the formula (iii-9) or the like.

A process for producing a N-sulfonyloxyimide compound represented by the general formula (3) will be discussed later.

[Sulfonic Acid Salt]

Sulfonic acid salt useful as a raw material compound for a sulfonic acid onium salt compound which is one of the photo-acid generator of the present invention is represented by the following general formula (4).

[Chemical Formula 46]

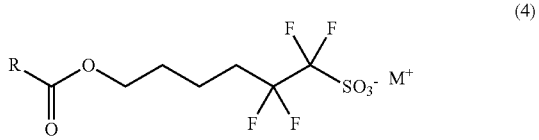
(4)

[In the general formula (4), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms. M represents Na, K or Li.]

The concrete structure of R in the general formula (4) is exemplified again by the concrete structure as exemplified by the general formula (1).

M as shown in the general formula (4) represents Na, K or Li, which is upon consideration of the convenience of synthesis and the easiness of isolation of sulfonic acid. It is possible to use metals other than those, such as calcium ion, magnesium ion and ammonium ion. The use of them is not particularly limited unless the sulfonic acid is able to stably exist.

In a case of using the sulfonic acid salt as the raw material for the above photo-acid generator, it is required only to bring R into coincident with R of the photo-acid generator.

[Sulfonyl Halide Compound]

A sulfonyl halide compound useful as a raw material compound for a N-sulfonyloxyimide compound which is one of the photo-acid generator of the present invention is represented by the following general formula (6).

[Chemical Formula 47]

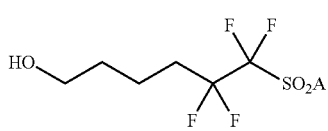
(6)

[In the general formula (6), A represents halogen atom.]

Examples of A as shown in the general formula (6) include fluorine, chlorine, bromine and iodine. Among these, chlorine and bromine are preferable, and chlorine is particularly preferable in view of easiness of synthesis.

[A Process for Producing Sulfonic Acid Onium Salt Compound]

A sulfonic acid onium salt compound represented by the following general formula (2)

[Chemical Formula 48]

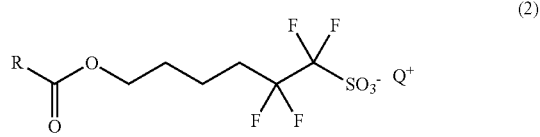
(2)

can be produced through four steps represented as follows (see Scheme 1).

A $1^{st}$ step: A step of sulfinating 6-bromo-5,5,6,6-tetrafluorohexan-1-ol by using a sulfinating agent thereby obtaining sulfinic acid salt represented by the following general formula (7).

[Chemical Formula 49]

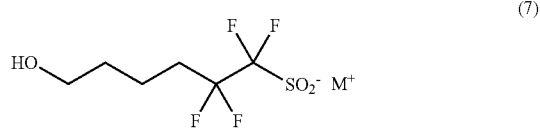
(7)

A $2^{nd}$ step: A step of oxidizing the sulfinic acid salt obtained by the Pt step and represented by the general formula (7) by using an oxidizing agent, thereby obtaining sulfonic acid salt represented by the following general formula (4).

[Chemical Formula 50]

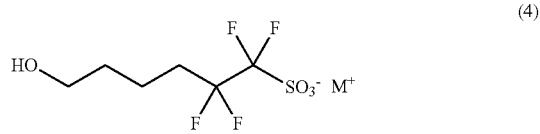
(4)

A $3^{rd}$ step: A step of reacting the sulfonic acid salt obtained by the $2^{nd}$ step and represented by the general formula (4) with a monovalent onium salt represented by the following general formula (8)

[Chemical Formula 51]

$Q^+X^-$ (8)

thereby obtaining a sulfonic acid onium salt represented by the following general formula (9).

[Chemical Formula 52]

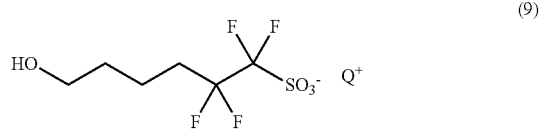
(9)

A 4th step: A step of reacting the sulfonic acid onium salt obtained by the 3rd step and represented by the general formula (9) with acid or acid halide represented by the following general formula (10)

[Chemical Formula 53]

(10)

or with acid anhydride represented by the following general formula (11)

[Chemical Formula 54]

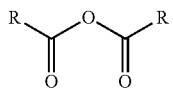

(11)

thereby obtaining a sulfonic acid onium salt compound represented by the general formula (2).

[In the general formula (2), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms. $Q^+$ represents a monovalent onium cation. In the general formula (7) and the general formula (4), M represents Na, K or Li. In the general formula (8), $Q^+$ has the same meaning as that of $Q^+$ in the general formula (2), while $X^-$ represents a monovalent anion. In the general formula (9), $Q^+$ has the same meaning as that of $Q^+$ in the general formula (2). In the general formula (10), $X^-$ represents hydroxyl group, fluorine atom, chlorine atom, bromine atom or iodine atom, while R has the same meaning as that of R in the general formula (2). R in the general formula (11) has the same meaning as that of R in the general formula (2).]

Hereinafter, each of the steps will be discussed in detail. First of all, the 1st step according to the present invention will be discussed. The 1st step is a step of sulfinating 6-bromo-5,5,6,6-tetrafluorohexan-1-ol by using a sulfinating agent thereby obtaining sulfinic acid salt represented by the following general formula (7) (a sulfination step).

As the sulfinating agent used in the present step, those represented by the following general formula (13)

[Chemical Formula 55]

$(S^1)_m(M^1)_n \cdot pH_2O$ (13)

(In the above general formula (13), $S^1$ represents $S_2O_4$, $HOCH_2SO_2$, $SO_4$ or $HSO_4$. m and n represent an integer. p represents 0 (zero) or an integer. $M^1$ represents Li, Na, K or $NH_4$.)

can be used. Concrete examples thereof include lithium dithionite, sodium dithionite, potassium dithionite, ammonium dithionite, lithium hydroxymethanesulfinate, sodium hydroxymethanesulfinate, potassium hydroxymethanesulfinate, ammonium hydroxymethanesulfinate, lithium sulfite, sodium sulfite, potassium sulfite, ammonium sulfite, lithium hydrogen sulfite, sodium hydrogen sulfite, potassium hydrogen sulfite and ammonium hydrogen sulfite. Among these, sodium dithionite and potassium dithionite are preferable, and sodium dithionite is particularly preferable.

The mole ratio of the sulfinating agent to 6-bromo-5,5,6,6-tetrafluorohexan-1-ol is 0.5 to 10 in general, preferably 0.9 to 5.0 and particularly preferably 1.0 to 2.0.

This reaction can be performed in air; however, the sulfinating agent is sometimes decomposed by water content in air. It is therefore preferable to perform the reaction in a nitrogen or argon atmosphere.

This reaction sometimes proceeds without the addition of bases; however, bases are usually added because the reaction can be accelerated with the addition of the same. Examples of the bases to be added include lithium carbonate, sodium carbonate, potassium carbonate, lithium hydrogencarbonate, sodium hydrogencarbonate and potassium hydrogencarbonate. The preferable are sodium hydrogencarbonate and potassium hydrogencarbonate.

This reaction is preferably conducted in a mixture solvent of an organic solvent and water. Examples of the organic solvent are those who have good compatibility with water, such as lower alcohols, tetrahydrofuran, N,N-dimethylformamide, N,N-dimethylacetamide, acetonitrile and dimethyl sulfoxide. The more preferable are N,N-dimethylacetamide, acetonitrile, dimethyl sulfoxide or the like. The particularly preferable is acetonitrile.

The ratio of the organic solvent to be used is not less than 5 parts by weight in general, preferably not less than 10 parts by weight, and more preferably 20 to 90 parts by weight relative to 100 parts by weight of total of the organic solvent and water.

The reaction temperature is 40 to 200° C. in general, preferably 60 to 100° C. The reaction time is 0.5 to 120 hours in general, preferably 2 to 72 hours; however, it is preferable to determine a temporal point at which the raw material 6-bromo-5,5,6,6-tetrafluorohexan-1-ol has been consumed as the endpoint of the reaction, by using an analytical device such as thin layer chromatography (TLC) and nuclear magnetic resonance (NMR). In a case where 6-bromo-5,5,6,6-tetrafluorohexan-1-ol is still not consumed upon spending the reaction time, a reaction solution is separated into two layers to discard a water layer, followed by the secondary additions of water, the sulfinating agent and the bases, thereby being able to restart the reaction. In a case where the reaction temperature is higher than the boiling point of the organic solvent or water, a heat-resistant vessel such as an autoclave is used.

By the way, in a case where a cation moiety of the sulfinating agent is identical with that of an inorganic base (e.g., "a case of using sodium dithionite as the sulfinating agent while using sodium carbonate as the inorganic base" or "a case of using potassium sulfite as the sulfinating agent while using potassium hydrogencarbonate as the inorganic base") it is possible to obtain sulfinic acid salt represented by the general formula (7) as a single product. In this case the reaction solution may be purified further by methods such as recrystallization, upon being subjected to a treatment such as condensation.

In a case where a cation moiety of the sulfinating agent is different from that of the inorganic base, sulfinic acid salt cannot be a single product in the strict sense but be a mixture of cation derived from the sulfinating agent and cation derived from the inorganic base, in the general formula (7). The ratio of cation is to vary according to the ratio between the used sulfinating agent and the used inorganic base and to reaction conditions. With such a mixture, purification by recrystallization or the like is made difficult in general. Such a cation mixture can be brought into the next step as it is however, analysis, purification and the like are made difficult thereby. Therefore, when using an inorganic base as the base, it is preferable to use a sulfinating agent and an inorganic base whose cation moieties are identical with each other.

Then, the $2^{nd}$ step according to the present invention will be discussed. The $2^{nd}$ step is a step of reacting the sulfinic acid salt obtained by the $1^{st}$ step and represented by the general formula (7) with an oxidizing agent, thereby obtaining sulfonic acid salt represented by the general formula (4) (an oxidation step).

An example of the oxidizing agent used in this step is hydrogen peroxide, and additionally methachloroperbenzoic acid, t-butyl hydroperoxide, potassium peroxydisulfate, potassium permanganate, sodium perborate, methasodium iodate, chromic acid, sodium dichromate, halogen, iodobenzene dichloride, iodobenzene diacetate, osmium oxide (VIII), ruthenium oxide (VIII), sodium hypochlorite, sodium chlorite, oxygen gas and ozone gas. Hydrogen peroxide, methachloroperbenzoic acid, t-butyl hydroperoxide and the like are preferable.

The mole ratio of the oxidizing agent to sulfinic acid salt represented by the general formula (7) is from 0.9 to 10.0 in general, and preferably from 1.0 to 2.0. In a case where the raw sulfinic acid salts are such a rough substance as to be unclear in exact molar amount, it is required only to add the oxidizing agent relative to the molar amount of 6-bromo-5,5,6,6-tetrafluorohexan-1-ol which is not yet sulfinated.

Furthermore, the oxidizing agent can be used in combination with a transition metal catalyst. Examples of the transition metal catalyst are disodium tungstate, iron chloride (III), ruthenium chloride (III) and selenium oxide (IV). The preferable is disodium tungstate.

The mole ratio of the transition metal catalyst to sulfinic acid salt represented by the general formula (7) is from 0.0001 to 1.0 in general, preferably from 0.001 to 0.5, and more preferably from 0.001 to 0.1.

Moreover, in addition to the oxidizing agent and the transition metal catalyst, a buffer solution may be used for the purpose of adjusting the pH of the reaction solution. Examples of the buffer include disodium hydrogenphosphate, sodium dihydrogenphosphate, dipotassium hydrogenphosphate and potassium dihydrogenphosphate. The mole ratio of the buffer to sulfinic acid salt represented by the general formula (7) is from 0.01 to 2.0 in general, preferably from 0.03 to 1.0 and more preferably from 0.05 to 0.5.

This reaction is conducted in a reaction solvent in general. Examples of the reaction solvent include water, and additionally an organic solvent such as lower alcohols, tetrahydrofuran, N,N-dimethylformamide, N,N-dimethylacetamide, acetonitrile, dimethyl sulfoxide, acetic acid and trifluoroacetic acid. The more preferable are water, methanol, N,N-dimethylacetamide, acetonitrile, dimethyl sulfoxide and the like. The particularly preferable are water and methanol.

Additionally, the organic solvent and water may be used in combination as necessary, in which case the ratio of the organic solvent to be used is not less than 5 parts by weight in general, preferably not less than 10 parts by weight and more preferably from 20 to 90 parts by weight relative to 100 parts by weight of total of the organic solvent and water. The amount of the reaction solvent to be used is from 1 to 100 parts by weight in general, preferably from 2 to 100 parts by weight and more preferably 5 to 50 parts by weight relative to 1 part by weight of sulfinic acid salt represented by the general formula (7).

The reaction temperature is from 0 to 100° C. in general, preferably from 5 to 60° C. and more preferably from 5 to 40° C. The reaction time is from 0.1 to 72 hours in general, preferably from 0.5 to 24 hours and more preferably from 0.5 to 12 hours; however, it is preferable that a temporal point at which sulfinic acid salt serving as the raw material and represented by the general formula (7) has been consumed is determined by an analytical device such as thin layer chromatography (TLC) and nuclear magnetic resonance (NMR), as the endpoint of the reaction.

Incidentally, the reaction solution may be brought into the next step only with such a degree of treatment as to be directly condensed.

Then, the $3^{rd}$ step according to the present invention will be discussed. The $3^{rd}$ step is a step of reacting the sulfonic acid salt obtained by the $2^{nd}$ step and represented by the general formula (4) with a monovalent onium salt represented by the following general formula (8)

[Chemical Formula 56]

$$Q^+X^- \qquad (8)$$

thereby obtaining sulfonic acid onium salt represented by the general formula (9) (an onium-salt exchanging step).

With regard to onium cation $Q^+$ included in the general formula (8), the same as $Q^+$ in the general formula (2) may be used. The particular structure is as discussed above.

Then, examples of a monovalent anion $X^-$ shown in the general formula (8) include $F^-$, $Cl^-$, $Br^-$, $I^-$, $ClO_4^-$, $HSO_4^-$, $H_2PO_4^-$, $BF_4^-$, $PF_6^-$, $SbF_6^-$, aliphatic sulfonic acid anion, aromatic sulfonic acid anion, trifluoromethanesulfonic acid anion, fluorosulfonic acid anion, aliphatic carboxylic acid anion, aromatic carboxylic acid anion, fluorocarboxylic acid anion and trifluoroacetic acid anion. The preferable are $Cl^-$, $Br^-$, $HSO_4^-$, $BF_4^-$, aliphatic sulfonic acid ion and the like. The more preferable are $Cl^-$, $Br^-$ and $HSO_4^-$.

The mole ratio of monovalent onium salt represented by the general formula (8) to sulfonic acid salt represented by the general formula (4) is from 0.5 to 10.0 in general, preferably from 0.8 to 2.0 and more preferably from 0.9 to 1.2.

This reaction is conducted in a reaction solvent in general. Preferable examples of the reaction solvent are organic solvents such as lower alcohols, tetrahydrofuran, N,N-dimethylformamide, N,N-dimethylacetamide, acetonitrile and dimethyl sulfoxide, in addition to water. The more preferable are water, methanol, N,N-dimethylacetamide, acetonitrile, dimethyl sulfoxide and the like. The particularly preferable is water.

Additionally, the organic solvent and water may be used in combination as necessary, in which case the ratio of the organic solvent to be used is not less than 5 parts by weight in general, preferably not less than 10 parts by weight, more preferably from 20 to 90 parts by weight relative to 100 parts by weight of total of the organic solvent and water. The amount of the reaction solvent to be used is from 1 to 100 parts by weight in general, preferably from 2 to 100 parts by weight, more preferably 5 to 50 parts by weight relative to 1 part by weight of a counter ion exchange precursor.

The reaction temperature is from 0 to 80° C. in general and preferably from 5 to 30° C. The reaction time is from 10 minutes to 16 hours in general and preferably from 30 minutes to 6 hours; however, it is preferable that a temporal point at which sulfonic acid salt represented by the general formula (4) and serving as the raw material has been consumed is determined by an analytical device such as thin layer chromatography (TLC) and nuclear magnetic resonance (NMR), as the endpoint of the reaction.

The thus obtained sulfonic acid onium salt represented by the general formula (9) can be rinsed with an organic solvent or can be extracted to be purified. The organic solvent are preferably organic solvent which are not to be mixed with water, so that examples thereof include esters such as ethyl acetate and n-butyl acetate, ethers such as diethyl ether, and halogenated alkyls such as methylene chloride and chloroform. Sulfinic acid onium salt represented by the general formula (9) may be purified by recrystallization, reprecipitation or the like, as necessary.

Then, 4$^{th}$ step of the present invention will be discussed. The 4$^{th}$ step is a step of reacting the sulfonic acid onium salt obtained by the 3$^{rd}$ step and represented by the general formula (9) with acid or acid halide represented by the general formula (10) or with acid anhydride represented by the general formula (11), thereby obtaining a sulfonic acid onium salt compound represented by the general formula (2) (an esterification step).

In the general formula (10) and the general formula (11), R represents a substituted or unsubstituted linear, branched or cyclic alkyl group having 1 to 20 carbon atoms, a substituted or unsubstituted aryl group having 6 to 15 carbon atoms, or heteroaryl group having 4 to 15 carbon atoms; however, the concrete structure thereof is exemplified again by the structure exemplified by the general formula (1). Additionally, in the general formula (10), X' represents hydroxyl group, fluorine atom, chlorine atom, bromine atom or iodine atom.

As a concrete process of producing sulfonic acid onium salt represented by the general formula (9) by reacting sulfonic acid onium salt represented by the general formula (9) and obtained by the 3$^{rd}$ step with carboxylic acid or carboxylic acid halide represented by the general formula (10) or with carboxylic acid anhydride represented by the general formula (11), any of the hitherto known esterification processes may be employed. There is no limit in particular.

An example of the esterification process includes: a process of causing dehydrogenating condensation between sulfonic acid onium salt represented by the general formula (9) and carboxylic acid represented by the general formula (10) (X'=OH) in the presence of an acid catalyst (Fisher's esterification synthetic reaction); and a process of reacting sulfonic acid onium salt represented by the general formula (9) with carboxylic acid halide (X'=Cl, Br, I, F) represented by the general formula (10) or with carboxylic acid anhydride represented by the general formula (11).

In a case of using carboxylic acid (X'=OH) represented by the general formula (10), the use amount of carboxylic acid represented by the general formula (10) is not particularly limited but from 0.1 to 5 moles in general, preferably from 0.2 to 3 moles, and more preferably from 0.5 to 2 moles relative to 1 mole of sulfonic acid onium salt represented by the general formula (9). It is particularly preferable that the use amount of carboxylic acid is from 0.8 to 1.5 moles.

In the reaction, an aprotic solvent such as dichloroethane, toluene, ethylbenzene, monochlorobenzene, acetonitrile and N,N-dimethylformamide is generally used. These solvents may be used singly and do not have any problems with being used in combination of not less than two kinds of these.

The reaction temperature is not particularly limited but within a range of from 0 to 200° C. in general, preferably from 20 to 180° C. and more preferably from 50 to 150° C. It is preferable to conduct the reaction while stirring.

The reaction time is from several minutes to 100 hours in general, preferably from 30 minutes to 50 hours and more preferably from 1 to 20 hours, though depending on the reaction temperature; however, it is preferable to determine a temporal point at which sulfonic acid onium salt serving as the raw material and represented by the general formula (9) has been consumed as the endpoint of the reaction, by using an analytical device such as gas chromatography (GC) and nuclear magnetic resonance (NMR).

In general, this reaction is conducted with the addition of an organic acid such as p-toluenesulfonic acid and/or an inorganic acid such as sulfuric acid, as an acid catalyst. Alternatively, 1,1'-carbonyldiimidazole, N,N'-dicyclohexylcarbodiimide or the like may be added as a dehydrating agent. The amount of the acid catalyst to be used is not particularly limited but preferably from 0.0001 to 10 moles, preferably from 0.001 to 5 moles and more preferably from 0.01 to 1.5 moles relative to 1 mole of sulfonic acid onium salt represented by the general formula (9).

It is preferable to conduct esterification reaction using the acid catalyst while carrying out dehydration, for example, with the use of Dean-Stark apparatus. This is because the reaction time tends to be shortened thereby.

By taking general means such as extraction, distillation and recrystallization after the termination of the reaction, a sulfonic acid onium salt compound represented by the formula (2) can be obtained. Moreover, it is possible to purify it by column chromatography, recrystallization or the like, as necessary.

On the other hand, in the case of using carboxylic acid halide (X'=Cl, Br, I, F) represented by the general formula (10) or carboxylic acid anhydride represented by the general formula (11), the amount of carboxylic acid halide represented by the general formula (10) or carboxylic acid anhydride represented by the general formula (11) to be used and made act on sulfonic acid onium salt represented by the general formula (9) is not particularly limited but from 0.1 to 5 moles in general, preferably from 0.2 to 3 moles and more preferably from 0.5 to 2 moles relative to 1 mole of sulfonic acid onium salt represented by the general formula (9). It is particularly preferable to use the carboxylic acid halide or the carboxylic acid anhydride in an amount of from 0.8 to 1.5 moles.

The reaction may be conducted in the absence of solvents or may be conducted in a non-reactive solvent. Such solvents are required only to be non-reactive and therefore not particularly limited. For example, the reaction may be conducted in water, an organic solvent or a mixture of these. Examples of the organic solvent include: hydrocarbon-based solvents such as n-hexane, benzene and toluene; ketone-based solvents such as acetone, methyl ethyl ketone and methyl isobutyl ketone; ester-based solvents such as ethyl acetate and butyl acetate; ether-based solvents such as diethyl ether, diethylene glycol dimethyl ether, tetrahydrofuran and dioxane; halogen-based solvents such as dichloromethane, chloroform, carbon tetrachloride, 1,2-dichloroethane, tetrachloroethylene, chlorobenzene and ortho-chlorobenzene; and polar solvents such as acetonitrile, N-dimethylformamide, N,N-dimethylimidazolidinone, dimethyl sulfoxide and sulfolane. These solvents may be used singly and do not have any problems with being used in combination of not less than two kinds of these.

The reaction temperature is not particularly limited but within a range of from −78 to 150° C. in general, preferably from −20 to 120° C. and more preferably from 0 to 100° C.

The reaction time depends also on the reaction temperature but it ranges from several minutes to 100 hours in general, preferably from 30 minutes to 50 hours and more preferably from 1 to 20 hours. However, it is preferable that a temporal point at which sulfonic acid onium salt serving as the raw material and represented by the general formula (9) has been consumed is determined by an analytical device such as gas chromatography (GC) and nuclear magnetic resonance (NMR), as the endpoint of the reaction.

In the case of using carboxylic acid halide represented by the general formula (10), the reaction may be conducted while removing a by-product hydrogen halide (e.g. hydrogen chloride) from the reaction system in the absence of catalysts, may be conducted with the use of the acid acceptor for receiving by-product acids in the case of using carboxylic acid anhydride represented by the general formula (11).

Examples of the acid acceptor include: organic bases such as triethylamine, pyridine, picoline, dimethylaniline, diethylaniline, 1,4-diazabicyclo[2.2.2]octane (DABCO) and 1,8-diazabicyclo[5.4.0]undec-7-ene (DBU); and inorganic bases such as sodium hydrogencarbonate, sodium carbonate, potassium carbonate, lithium carbonate, sodium hydroxide, potassium hydroxide, calcium hydroxide and magnesium oxide. The amount of the acid acceptor to be used is not particularly limited but ranges from 0.05 to 10 moles, preferably from 0.1 to 5 moles and more preferably from 0.5 to 3 moles relative to 1 mole of sulfonic acid onium salt represented by the general formula (9).

By taking normal means such as extraction, distillation and recrystallization after the termination of the reaction, a sulfonic acid onium salt compound can be obtained. Moreover, it may be purified by column chromatography, recrystallization or the like, as necessary.

[Production Process for N-Sulfonyloxyimide Compound]

A N-sulfonyloxyimide compound represented by the general formula (3)

[Chemical Formula 57]

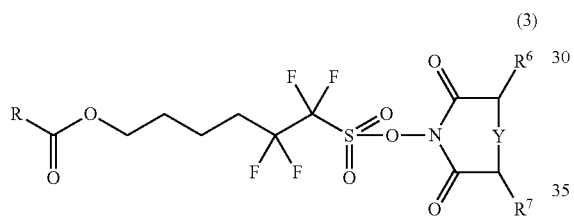

(3)

can be produced through four steps as will be discussed below (see Scheme 2). [In the general formula (3), R represents a substituted or unsubstituted linear or branched monovalent hydrocarbon group having 1 to 30 carbon atoms, a substituted or unsubstituted monovalent hydrocarbon group having a cyclic or a partially cyclic structure and having 3 to 30 carbon atoms, a substituted or unsubstituted aryl group having 6 to 30 carbon atoms, or a substituted or unsubstituted monovalent heterocyclic organic group having 4 to 30 carbon atoms. X' represents hydroxyl group, fluorine atom, chlorine atom, bromine atom or iodine atom. A represents halogen atom. $R^6$ and $R^7$ mutually independently represent hydrogen atom or a substituted or unsubstituted monovalent organic group; alternatively, $R^6$ and $R^7$ form a ring together with the carbon atoms to which they bond mutually. Y represents a single bond, a double bond or a divalent organic group.]

A $1^{st}$ step: A step of sulfinating 6-bromo-5,5,6,6-tetrafluorohexan-1-ol by using a sulfinating agent thereby obtaining sulfinic acid salt represented by the following general formula (7) (a sulfination step).

[Chemical Formula 58]

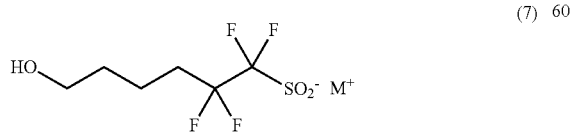

(7)

A $2^{nd}$ step: A step of halogenating the sulfinic acid salt obtained by the $1^{st}$ step and represented by the general formula (7) by using a halogenating agent, thereby obtaining a sulfonyl halide compound represented by the following general formula (6).

[Chemical Formula 59]

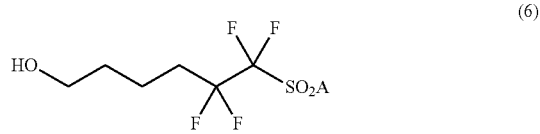

(6)

[In the general formula (6), A represents halogen atom.]

A $3^{rd}$ step: A step of reacting the sulfonyl halide compound obtained by the $2^{nd}$ step and represented by the general formula (6) with acid or acid halide represented by the following general formula (10)

[Chemical Formula 60]

(10)

or with acid anhydride represented by the following general formula (11)

[Chemical Formula 61]

(11)

thereby obtaining a sulfonyl halide compound represented by the following general formula (14).

[Chemical Formula 62]

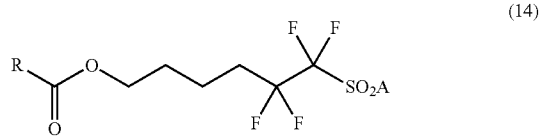

(14)

[In the general formula (14), R has the same meaning as that of R in the general formula (3). A has the same meaning as that of A in the general formula (6).]

A $4^{th}$ step: A step of reacting the sulfonyl halide compound obtained by the $3^{rd}$ step and represented by the general formula (14) with N-hydroxydicarboxyimide represented by the following general formula (12)

[Chemical Formula 63]

(12)

thereby obtaining a N-sulfonyloxyimide compound represented by the general formula (3).

[In the general formula (12), $R^6$ and $R^7$ mutually independently represent hydrogen atom or a substituted or unsubstituted monovalent organic group; alternatively, $R^6$ and $R^7$ form a ring together with the carbon atoms to which they bond mutually. Y represents a single bond, a double bond or a divalent organic group.]

Hereinafter, each of the steps will be discussed in detail. The $1^{st}$ step or a sulfination step is as had been discussed with the $1^{st}$ step of the production process for the above-mentioned sulfonic acid onium salt compound.

With regard to the $2^{nd}$ step or a halogenation step, any of the hitherto known halogenation processes may be employed. There is no limit in particular. Among the halogenations, chlorination is a convenient process.

A reaction made between the sulfinic acid salt represented by the general formula (7) and a chlorinating agent may be conducted, for example, in conformance with a general process as discussed in "D. D. DesMarteau, Inorganic Chemistry, Vol. 32, 5007, 1993". At the time of the reaction, a method of blowing chlorine gas into the reaction solution can be used, for example.

At the time of the reaction, the amount of the chlorinating agent to be used is enormously excessive relative to sulfinic acid salt represented by the general formula (7), in general.

This reaction is conducted in a reaction solvent in general. Examples of the reaction solvent include water, and preferably organic solvents such as tetrahydrofuran, N,N-dimethylformamide, N,N-dimethylacetamide, acetonitrile and dimethyl sulfoxide. The more preferable are organic solvents including water, methanol, N,N-dimethylacetamide, acetonitrile, dimethyl sulfoxide and the like. The particularly preferable is water.

The amount of the reaction solvent to be used is from 5 to 100 parts by weight in general, preferably from 10 to 100 parts by weight, and more preferably from 20 to 50 parts by weight relative to 100 parts by weight of sulfinic acid salt represented by the general formula (7). Additionally, the organic solvent and water may be used in combination as necessary, in which case the ratio of the organic solvent to be used is from 5 to 100 parts by weight in general, preferably from 10 to 100 parts by weight and more preferably from 20 to 90 parts by weight relative to 100 parts by weight of total of the organic solvent and water.

The reaction temperature is from 0 to 100° C. in general, preferably from 5 to 60° C. and more preferably from 5 to 40° C. The reaction time is from 5 minutes to 12 hours in general, and preferably from 10 minutes to 5 hours; however, it is preferable to determine a temporal point at which sulfinic acid salt serving as the raw material and represented by the general formula (7) has been consumed as the endpoint of the reaction, by using an analytical device such as nuclear magnetic resonance (NMR).

The thus obtained sulfonyl halide compound represented by the general formula (6) may be purified by distillation or recrystallization, as necessary.

Then, concerning the $3^{rd}$ step or an esterification step, it can be performed in the same manner as the process as had been discussed with the $4^{th}$ step of the production process for the above-mentioned sulfonic acid onium salt compound. However, a sulfonyl halide compound represented by the general formula (6) is so highly reactive as to easily cause self-condensation, so that a process of causing dehydrogenating condensation by using carboxylic acid represented by the general formula (10) (X'=OH) in the presence of an acid catalyst (Fisher's esterification synthetic reaction) is exclusively difficult. Therefore, the preferable is a process in which carboxylic acid halide (X'=Cl, Br, I, F) represented by the general formula (10) or carboxylic acid anhydride represented by the general formula (11) is used.

The $4^{th}$ step is a step of reacting the sulfonyl halide compound obtained by the $3^{rd}$ step and represented by the general formula (14) with N-hydroxydicarboxyimide represented by the general formula (12) in a reaction solvent and in the presence of a basic catalyst.

At the time of reaction, the mole ratio of a N-hydroxydicarboxylmide compound relative to a sulfonyl halide compound represented by the general formula (14) is 0.1 to 10.0 in general, preferably from 0.3 to 5.0, and more preferably from 0.5 to 2.0.

This reaction is conducted in a reaction solvent in general. Preferable examples of the reaction solvent include organic solvents such as acetonitrile, dimethylformamide, tetrahydrofuran, dimethyl sulfoxide, methylene chloride, methylene bromide and chloroform. The more preferable are acetonitrile, tetrahydrofuran and methylene chloride.

The amount of the reaction solvent to be used relative to 100 parts by weight of a sulfonyl halide compound represented by the general formula (14) is from 5 to 100 parts by weight in general, preferably from 10 to 100 parts by weight and more preferably 20 to 50 parts by weight.

Preferable examples of the basic catalysts are triethylamine, pyridine, N,N-di-i-propyl ethylamine, 2,6-lutidine, N,N-diethylaniline, 4-dimethylaminopyridine and diazabicycloundecene. The more preferable are triethylamine, 4-dimethylaminopyridine and the like.

The mole ratio of the basic catalyst relative to a sulfonyl halide compound represented by the general formula (14) is 1.0 to 10.0 in general, preferably from 1.5 to 5.0, and more preferably from 1.5 to 3.0.

The reaction temperature is from 0 to 80° C. in general, preferably from 5 to 30° C. The reaction time is from 5 minutes to 6 hours in general and preferably from 10 minutes to 2 hours; however, it is preferable to determine a temporal point at which a sulfonyl halide compound represented by the general formula (14) and serving as the raw material has been consumed as the endpoint of the reaction, by using an analytical device such as gas chromatography (GC) and nuclear magnetic resonance (NMR).

By taking general means such as extraction, distillation and recrystallization after the termination of the reaction, a N-sulfonyloxyimide compound represented by the general formula (3) can be obtained. Moreover, it is possible to purify it by column chromatography, recrystallization or the like, as necessary.

EXAMPLES

Hereinafter, the present invention will be more specifically discussed with reference to the following Examples; however, the present invention is not limited by these Examples. Incidentally, In the following description, all "part" and "%" in Examples, Comparative Examples and Reference Examples are by mass unless otherwise specified.

Synthesis of Sulfonic Acid Onium Salt

Example 1-1

Production of 2-(4-Bromo-3,3,4,4-Tetrafluorobutyl)-Malonic Acid Diethyl Ester

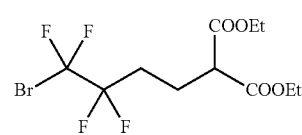

[Chemical Formula 64]

In nitrogen atmosphere, 1900 mL of dimethylformamide was prepared with the addition of 320 g (7.17 mol) of sodium hydride (60% mineral oil-containing product), followed by putting it in an iced bath with the addition of 1208 g (7.17 mol) of diethyl malonate. After 1 hour of stirring, 2400 g (7.17 mol) of 1-bromo-1,1,2,2-tetrafluoro-4-iodobutane was added to this solution while regulating the reaction solution so as to be not higher than 100° C. After 1 hour of stirring, 1000 mL of 1N hydrochloric acid was added thereto, followed by extracting it with diisopropyl ether. Then, an organic layer was concentrated, followed by distillation under reduced pressure (115-116° C./0.53 kPa), thereby obtaining 1940 g of the objective 2-(4-bromo-3,3,4,4-tetrafluorobutyl)-malonic acid diethyl ester (74% yield, 89% GC purity) in the form of a light yellow liquid.

Properties of
2-(4-Bromo-3,3,4,4-Tetrafluorobutyl)-Malonic Acid Diethyl Ester $^1$H NMR (Solvent for measurement: Deuterated chloroform, Reference material: Tetramethylsilane) δ (ppm): 1.23 (6H, t, J=7.1 Hz), 2.05-2.18 (2H, m), 2.20-2.40 (2H, m), 3.59 (1H, t, J=7.0 Hz), 4.00-4.22 (4H, m).

$^{19}$F NMR (Solvent for measurement: Deuterated chloroform, Reference material: Trichlorofluoromethane) δ (ppm): −66.2 (2F, s), −112.0 (2F, brt, J=18 Hz).

Example 1-2

Production of 6-Bromo-5,5,6,6-Tetrafluorohexanoic Acid

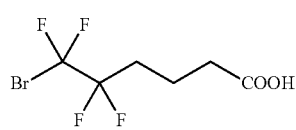

[Chemical Formula 65]

7000 g (26.4 mol) of 15% of sodium hydroxide aqueous solution was added to 1940 g (5.29 mol) of the objective 2-(4-bromo-3,3,4,4-tetrafluorobutyl)-malonic acid diethyl ester obtained as discussed above, followed by refluxing it for 2 hours. Upon cooling it to room temperature, 2900 g (29.1 mol) of concentrated hydrochloric acid (36%) is added in an iced bath, followed by extraction with diisopropyl ether. A residue obtained by distilling a solvent off was heated to 170° C. thereby obtaining 1338 g of the objective 6-bromo-5,5,6,6-tetrafluorohexanoic acid (95% yield) in the form of a brown liquid.

Properties of 6-Bromo-5,5,6,6-Tetrafluorohexanoic Acid $^1$H NMR (Solvent for measurement: Deuterated chloroform, Reference material: Tetramethylsilane) δ (ppm): 1.86-1.99 (2H, m), 2.05-2.24 (2H, m), 2.42-2.52 (2H, m).

$^{19}$F NMR (Solvent for measurement: Deuterated chloroform, Reference material: Trichlorofluoromethane) δ (ppm): −66.2 (2F, s), −112.6 (2F, brdd, J=18 Hz, 15 Hz).

Example 1-3

Production of 6-Bromo-5,5,6,6-Tetrafluorohexanoyl Chloride

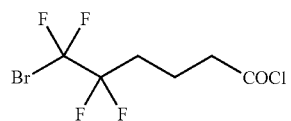

[Chemical Formula 66]

In nitrogen atmosphere, 780 g (6.33 mol) of thionyl chloride was added to 1300 g (4.87 mol) of the 6-bromo-5,5,6,6-tetrafluorohexanoic acid obtained as discussed above, followed by stirring at 50° C. for 4 hours. Then distillation was conducted under reduced pressure thereby obtaining 1223 g of the objective 6-bromo-5,5,6,6-tetrafluorohexanoyl chloride in the form of a light yellow liquid (88% yield, 91% GC purity).

Properties of 6-Bromo-5,5,6,6-Tetrafluorohexanoyl Chloride $^1$H NMR (Solvent for measurement: Deuterated chloroform, Reference material: Tetramethylsilane) δ (ppm): 1.97-1.05 (2H, m), 2.09-2.24 (2H, m), 3.02 (2H, t, J=7.1 Hz).

$^{19}$F NMR (Solvent for measurement: Deuterated chloroform, Reference material: Trichlorofluoromethane) δ (ppm): −66.4 (2F, brs), −112.6 (2F, brdd, J=21 Hz, 9 Hz).

Example 1-4

Production of
6-Bromo-5,5,6,6-Tetrafluorohexan-1-ol

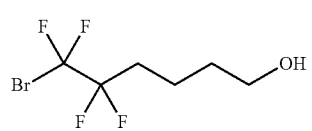

[Chemical Formula 67]

In nitrogen atmosphere, 500 g (1.75 mol) of 6-bromo-5,5,6,6-tetrafluorohexanoyl chloride was dissolved in 1500 mL of ethylene glycol dimethyl ether, followed by the addition of 53 g (1.40 mol) of sodium borohydride. Upon stirring it at 50° C. for 2 hours, a reaction solution was added to a diluted sulfuric acid aqueous solution, followed by extraction with diisopropyl ether. (At this time, the reaction solution was analyzed by gas chromatography, thereby confirming that the production ratio of the objective product 6-bromo-5,5,6,6-tetrafluorohexan-1-ol to the by-product 5,5,6,6-tetrafluorohexan-1-ol was 100%:0%. See Table 1.) After distilling a solvent off, distillation under reduced pressure (113° C./3.8 kPa) was conducted, thereby obtaining 332 g of the objective 6-bromo-5,5,6,6-tetrafluorohexan-1-ol in the form of a colorless transparent liquid (94% yield, 99.3% GC purity).

Properties of 6-Bromo-5,5,6,6-Tetrafluorohexan-1-ol $^1$H NMR (Solvent for measurement: Deuterated chloroform, Reference material: Tetramethylsilane) δ (ppm): 1.53-1.67 (4H, m), 1.98-2.10 (2H, m), 3.60 (2H, t, J=6.1 Hz).
$^{19}$F NMR (Solvent for measurement: Deuterated chloroform, Reference material: Trichlorofluoromethane) δ (ppm): −66.1 (2F, s), −112.6 (2F, t, J=16 Hz).

Example 1-5

Production of Sodium 1,1,2,2-Tetrafluoro-6-Hydroxy-Hexane-1-Sulfinic Acid

[Chemical Formula 68]

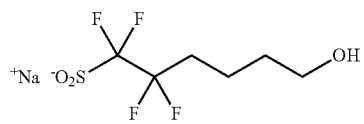

(7-a)

A glass flask equipped with a thermometer and a condenser was charged with 100 g (0.39 mol) of 1-bromo-1,1,2,2-tetrafluorohexanol, 52.4 g (0.62 mol) of sodium hydrogencarbonate, 94.0 g (0.54 mol) of sodium dithionite, 350 ml of acetonitrile and 350 ml of water, followed by stirring at 55° C. for 4 hours. After confirming the termination of the reaction by $^{19}$F NMR, cooling was conducted to room temperature, followed by separating an organic layer from two layers that a reaction solution had. Then, condensation and drying were conducted on the organic layer, thereby obtaining 120 g of sodium 1,1,2,2-tetrafluoro-6-hydroxyhexane-1-sulfinic acid (hereinafter referred to as "a compound (7-a)") in the form of white solid (67% yield, 56% purity).

Properties of Sodium 1,1,2,2-Tetrafluoro-6-Hydroxyhexane-1-Sulfinic Acid $^1$H NMR (Solvent for measurement: Deuterated dimethyl sulfoxide, Reference material: Tetramethylsilane) δ (ppm): 3.37-3.36 (t, 2H), 2.21-2.08 (m, 2H), 1.51-1.41 (m, 4H).
$^{19}$F NMR (Solvent for measurement: Deuterated dimethyl sulfoxide, Reference material: Trichlorofluoromethane) δ (ppm): −111.2 (s, 2F), −130.3 (s, 2F).

Example 1-6

Production of Sodium 1,1,2,2-Tetrafluoro-6-Hydroxy-Hexane-1-Sulfonic Acid

[Chemical Formula 69]

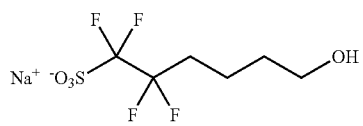

(4-a)

A glass flask equipped with a thermometer, a condenser and a dropping funnel was charged with 110 g (0.23 mol) of a compound (7-a) of 56% purity, a catalytic amount of sodium tungstate(IV) dehydrate and 200 ml of water, followed by stirring. Then, 44.0 g (0.39 mol) of 30% hydrogen peroxide solution triethylamine was added dropwise thereto, in an iced bath. After the termination of the dropping, stirring was continuously conducted for 1 hour, followed by confirming the termination of the reaction by $^{19}$F NMR. Then, a reaction solution was condensed, followed by rinsing it with 200 ml of diisopropyl ether. Then, filtration was conducted thereby obtaining a solid. The solid was then dried, thereby obtaining 93.8 g of sodium 1,1,2,2-tetrafluoro-6-hydroxyhexane-1-sulfonic acid (hereinafter referred to as "a compound (4-a)") in the form of a white solid (>99% yield, 67% purity).

Properties of Sodium 1,1,2,2-Tetrafluoro-6-Hydroxyhexane-1-Sulfonic Acid $^1$H NMR (Solvent for measurement: Deuterated dimethyl sulfoxide, Reference material: Tetramethylsilane) δ (ppm): 3.36 (t, 2H), 2.14 (m, 2H), 1.46 (m, 4H).
$^{19}$F NMR (Solvent for measurement: Deuterated dimethyl sulfoxide, Reference material: Trichlorofluoromethane) δ (ppm): −111.8 (s, 2F), −117.2 (s, 2F).

Example 1-7

Production of Triphenylsulfonium 1,1,2,2-Tetrafluoro-6-Hydroxy-Hexane-1-Sulfonate

[Chemical Formula 70]

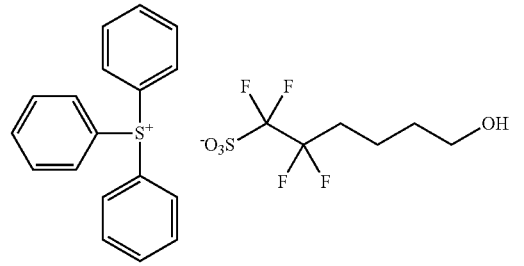

(9-a)

A glass flask equipped with a thermometer was charged with 90.0 g (0.21 mol) of a compound (4-a) of 67% purity and 350 ml of chloroform, followed by stirring. Then, an aqueous solution formed of 65.7 g (0.22 mol) of triphenylsulfonium chloride and 350 ml of water was added to this solution, followed by stirring for 1 hour. Subsequently, an organic layer of a reaction solution separated into two layers was rinsed with 300 ml of water five times. A solvent for the organic layer was distilled off up to about 50%, thereby obtaining 157 g of triphenylsulfonium 1,1,2,2-tetrafluoro-6-hydroxy-hexane-1-sulfonate (hereinafter referred to as "a compound (9-a)") in the form of 58% chloroform solution (84% yield, 58% purity).

Properties of Triphenylsulfonium 1,1,2,2-Tetrafluoro-6-Hydroxy-Hexane-1-Sulfonate $^1$H NMR (Solvent for measurement: Deuterated chloroform, Reference material: Tetramethylsilane) δ (ppm): 7.72-7.61 (m, 15H), 3.49 (t, 2H), 2.26-2.14 (m, 2H), 1.58-1.43 (m, 4H).
$^{19}$F NMR (Solvent for measurement: Deuterated chloroform, Reference material: Trichlorofluoromethane) δ (ppm): −112.90-112.98 (m, 2F), −117.6 (s, 2F).

Example 1-8

Production of Triphenylsulfonium 1,1,2,2-Tetrafluoro-6-(1-Adamantanecarbonyloxy)Hexane-1-Sulfonate

[Chemical Formula 71]

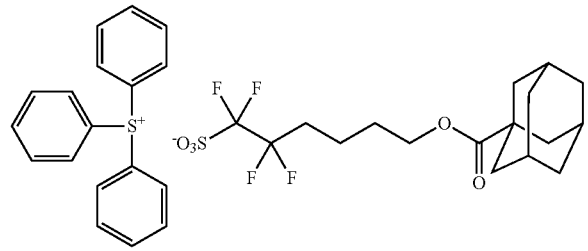

(A-1)

A glass flask equipped with a thermometer, a condenser and a dropping funnel was charged with 150 g (0.16 mol) of 58% chloroform solution of a compound (9-a), 63.5 g (0.32 mol) of 1-adamantanecarbonyl chloride and 350 ml of chloroform, followed by stirring. Then, 62.7 g (0.62 mol) of triethylamine was added dropwise thereto, in an iced bath. After the termination of the dropping, stirring was conducted at room temperature for 12 hours, followed by confirming the termination of the reaction by $^{19}$F NMR. Subsequently, 300 ml of water was added to a reaction solution, followed by removing a water layer. The obtained organic layer was rinsed with 300 ml of water 4 times and then condensed. The further obtained brown liquid was rinsed with 200 ml of diisopropyl ether 3 times. This was dissolved in 100 ml of chloroform, and thereafter added dropwise to 500 ml of diisopropyl ether to which a seed crystal was added. After conducting filtration on this solution, a solid was dried, thereby obtaining 90 g of triphenylsulfonium 1,1,2,2-tetrafluoro-6-(1-adamantanecarbonyloxy)hexane-1-sulfonate (83% yield, 98% purity). This compound will be referred to as "an acid generator (A-1)".

Properties of Triphenylsulfonium 1,1,2,2-Tetrafluoro-6-(1-Adamantanecarbonyloxy)Hexane-1-Sulfonate $^1$H NMR (Solvent for measurement: Deuterated chloroform, Reference material: Tetramethylsilane) δ (ppm): 7.75-7.65 (m, 15H), 4.02-3.99 (m, 2H), 2.39-2.34 (m, 2H), 1.97 (s, 3H), 1.84 (s, 6H), 1.66 (s, 6H), 1.63 (d, 4H).
$^{19}$F NMR (Solvent for measurement: Deuterated chloroform, Reference material: Trichlorofluoromethane) δ (ppm): -113.9-114.1 (m, 2F), -118.2 (s, 2F).

Example 2-1

Production of Diphenyliodonium 1,1,2,2-Tetrafluoro-6-Hydroxy-Hexane-1-Sulfonate

[Chemical Formula 72]

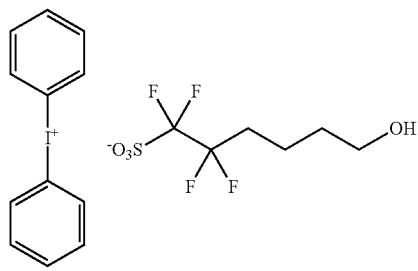

(9-b)

A glass flask equipped with a thermometer was charged with 90.0 g (0.21 mol) of 67% purity compound (4-a) and 350 ml of chloroform, followed by stirring. Then, 69.0 g (0.22 mol) of diphenyliodonium chloride and 350 ml of water were added to this solution, followed by stirring for 1 hour. Subsequently, an organic layer of a reaction solution separated into two layers was rinsed with 300 ml of water 5 times. A solvent for the organic layer was distilled off up to about 50%, thereby obtaining 160 g of diphenyliodonium 1,1,2,2-tetrafluoro-6-hydroxy-hexane-1-sulfonate (hereinafter referred to as "a compound (9-b)") in the form of 60% chloroform solution (82% yield, 60% purity).

Properties of Diphenyliodonium 1,1,2,2-Tetrafluoro-6-Hydroxy-Hexane-1-Sulfonate $^1$H NMR (Solvent for measurement: Deuterated chloroform, Reference material: Tetramethylsilane) δ (ppm): 7.73-7.60 (m, 10H), 3.48 (t, 2H), 2.26-2.13 (m, 2H), 1.59-1.44 (m, 4H).
$^{19}$F NMR (Solvent for measurement: Deuterated chloroform, Reference material: Trichlorofluoromethane) δ (ppm): -112.92-112.97 (m, 2F), -117.2 (s, 2F).

Example 2-2

Production of Diphenyliodonium 1,1,2,2-Tetrafluoro-6-(1-Adamantanecarbonyloxy)Hexane-1-Sulfonate

[Chemical Formula 73]

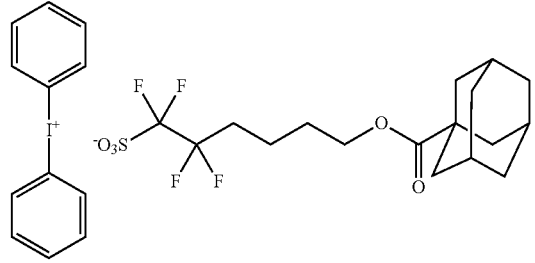

(A-2)

A glass flask equipped with a thermometer, a condenser and a dropping funnel was charged with 160 g (0.18 mol) of 60% chloroform solution of a compound (9-b), 1.4 g (0.36 mol) of 1-adamantanecarbonyl chloride and 350 ml of chloroform, followed by stirring. Then, 65.7 g (0.65 mol) of triethylamine was added dropwise thereto, in an iced bath. After the termination of the dropping, stirring was conducted at room temperature for 12 hours, followed by confirming the termination of the reaction by $^{19}$F NMR. Subsequently, 300 ml of water was added to a reaction solution, followed by removing a water layer. The obtained organic layer was rinsed with 300 ml of water 4 times and then condensed. The further obtained brown liquid was rinsed with 200 ml of diisopropyl ether 3 times. This was dissolved in 100 ml of chloroform, and thereafter added dropwise to 500 ml of diisopropyl ether to which a seed crystal was added. After conducting filtration on this solution, a solid was dried, thereby obtaining 110 g of diphenyliodonium 1,1,2,2-tetrafluoro-6-(1-adamantanecarbonyloxy)hexane-1-sulfonate (85% yield, 97% purity). This compound will be referred to as "an acid generator (A-2)".

Properties of Diphenyliodonium 1,1,2,2-Tetrafluoro-6-(1-Adamantanecarbonyloxy)Hexane-1-Sulfonate $^1$H NMR (Solvent for measurement: Deuterated chloroform, Reference material: Tetramethylsilane) δ (ppm): 7.73-7.60 (m, 10H), 4.02-4.00 (m, 2H), 2.38-2.33 (m, 2H), 1.98 (s, 3H), 1.83 (s, 6H), 1.66 (s, 6H), 1.62 (d, 4H).

$^{19}$F NMR (Solvent for measurement: Deuterated chloroform, Reference material: Trichlorofluoromethane) δ (ppm): −114.0-114.1 (m, 2F), −118.3 (s, 2F).

Example 3

Production of Triphenylsulfonium 1,1,2,2-Tetrafluoro-6-Acetoxyhexane-1-Sulfonate

[Chemical Formula 74]

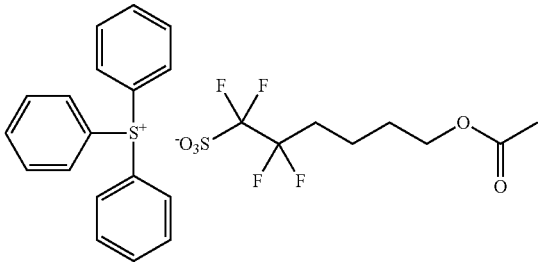

(A-3)

The same procedure as Example 1-8 was conducted with the use of 15 g (0.016 mol) of 58% chloroform solution of a compound (9-a) and 2.5 ml (0.035 mol) of acetyl chloride. As a result, there was obtained 8.29 g of triphenylsulfonium 1,1,2,2-tetrafluoro-6-acetoxyhexane-1-sulfonate in the form of a light brown viscous liquid (90% yield, 97% purity). This compound will be referred to as "an acid generator (A-3)".

Properties of Triphenylsulfonium 1,1,2,2-Tetrafluoro-6-Acetoxyhexane-1-Sulfonate $^1$H NMR (Solvent for measurement: Deuterated chloroform, Reference material: Tetramethylsilane) δ (ppm): 7.65-7.55 (m, 15H), 3.51 (t, 2H), 2.23-2.13 (m, 2H), 1.97 (s, 3H), 1.67-1.49 (m, 4H).

$^{19}$F NMR (Solvent for measurement: Deuterated chloroform, Reference material: Trichlorofluoromethane) δ (ppm): −114.2-114.4 (m, 2F), −117.9 (m, 2F).

Example 4

Production of Triphenylsulfonium 1,1,2,2-Tetrafluoro-6-(o-Hydroxybenzoyloxy)-1-Sulfonate

[Chemical Formula 75]

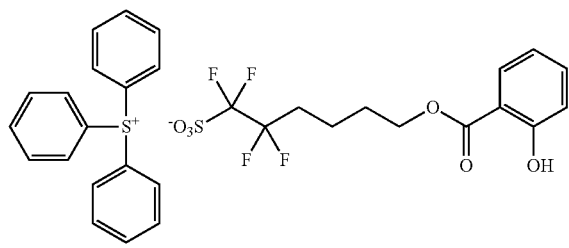

(A-4)

The same procedure as Example 1-8 was conducted with the use of 15 g (0.016 mol) of 58% chloroform solution of a compound (9-a) and 5.0 g (0.032 mol) of (o-hydroxy)benzoyl chloride. As a result, there was obtained 7.8 g of triphenylsulfonium 1,1,2,2-tetrafluoro-6-(o-hydroxybenzoyloxy)-1-sulfonate in the form of a light brown solid (75% yield, 98% purity). This compound will be referred to as "an acid generator (A-4)".

Properties of Triphenylsulfonium 1,1,2,2-Tetrafluoro-6-(o-Hydroxybenzoyloxy)-1-Sulfonate $^1$H NMR (Solvent for measurement: Deuterated chloroform, Reference material: Tetramethylsilane) δ (ppm): 7.78-7.76 (m, 1H), 7.72-7.62 (m, 15H), 7.41-7.36 (m, 1H), 6.89-7.37 (m, 1H), 6.80-6.76 (m, 1H), 3.49 (t, 2H), 4.56 (t, 2H), 2.92-2.77 (m, 2H), 1.77-1.56 (m, 4H).

$^{19}$F NMR (Solvent for measurement: Deuterated chloroform, Reference material: Trichlorofluoromethane) δ (ppm): −112.7 (s, 2F), −118.8 (s, 2F).

Example 5

Production of Triphenylsulfonium 1,1,2,2-Tetrafluoro-6-(p-Hydroxybenzoyloxy)-1-Sulfonate

[Chemical Formula 76]

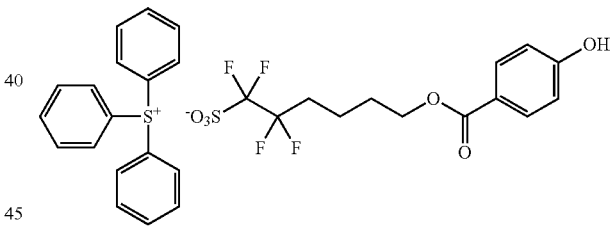

(A-5)

The same procedure as Example 1-8 was conducted with the use of 15 g (0.016 mol) of 58% chloroform solution of a compound (9-a) and 5.0 g (0.032 mol) of (p-hydroxy)benzoyl chloride. As a result, there was obtained 7.0 g of triphenylsulfonium 1,1,2,2-tetrafluoro-6-(o-hydroxybenzoyloxy)-1-sulfonate in the form of a light brown solid (67% yield, 97% purity). This compound will be referred to as "an acid generator (A-5)".

Properties of Triphenylsulfonium 1,1,2,2-Tetrafluoro-6-(o-Hydroxybenzoyloxy)-1-Sulfonate $^1$H NMR (Solvent for measurement: Deuterated chloroform, Reference material: Tetramethylsilane) δ (ppm): 7.88 (d, 2H), 7.73-7.61 (m, 15H), 6.82 (d, 2H), 3.49 (t, 2H), 4.56 (t, 2H), 2.92-2.77 (m, 2H), 1.77-1.56 (m, 4H).

$^{19}$F NMR (Solvent for measurement: Deuterated chloroform, Reference material: Trichlorofluoromethane) δ (ppm): −112.5 (s, 2F), −118.5 (s, 2F).

Synthesis of N-Sulfonyloxyimide

Example 6-1

Production of 1,1,2,2-Tetrafluoro-6-Hydroxy-Hexane-1-Sulfonyl Chloride

[Chemical Formula 77]

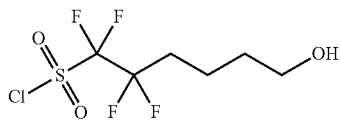

(6-a)

A 1 l flask with eggplant shape was charged with a solution formed by dissolving 50 g (0.108 mol) of a compound (7-a) of 56% purity in 150 ml of water, followed by bubbling the solution with an excessive amount of chlorine gas while stirring at room temperature. Then, an oily product that remained at the bottom of the flask was extracted with chloroform. An organic layer was rinsed with an aqueous solution of sodium hydrogencarbonate, followed by drying it with anhydrous magnesium sulfate. Thereafter, distillation was conducted under reduced pressure to remove chloroform, thereby obtaining 24.7 g of 1,1,2,2-tetrafluoro-6-hydroxy-hexane-1-sulfonyl chloride (hereinafter referred to as "a compound (6-a)") (80% yield, 95% purity).

Properties of 1,1,2,2-Tetrafluoro-6-Hydroxy-Hexane-1-Sulfonyl Chloride $^1$H NMR (Solvent for measurement: Deuterated chloroform, Reference material: Tetramethylsilane) δ (ppm): 3.50 (t, 2H), 2.25-2.13 (m, 2H), 1.57-1.43 (m, 4H).

$^{19}$F NMR (Solvent for measurement: Deuterated chloroform, Reference material: Trichlorofluoromethane) δ (ppm): −112.85-112.93 (m, 2F), −117.4 (s, 2F).

Example 6-2

Production of N-(1,1,2,2-Tetrafluoro-6-Hydroxy-Hexane-1-Sulfonyloxy)-5-Norbornene-2,3-Dicarboxyimide

[Chemical Formula 78]

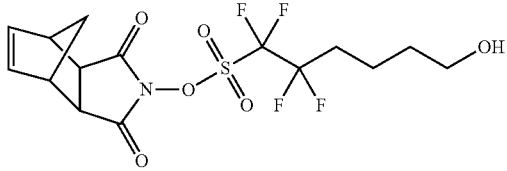

(13-a)

Then, 15 g (0.084 mol) of N-hydroxy-5-norbornene-2,3-dicarboxyimide was added to a solution formed by dissolving 20 g (0.070 mol) of 95% purity compound (6-a) in 100 g of tetrahydrofuran, followed by dropwise addition of 14.2 g (0.140 mol) of triethylamine. Thereafter, a reaction solution was stirred at room temperature for 30 minutes, followed by dropwise addition of water, thereby precipitating a reaction product out thereof as a white crystal. Thereafter, the precipitated substance was subjected to filtration and then dissolved in chloroform, followed by rinsing the solution sequentially with an aqueous solution of sodium hydrogencarbonate, 5% aqueous solution of hydrochloric acid and water. Thereafter, the solution was dried with anhydrous magnesium sulfate and then subjected to distillation under reduced pressure to remove chloroform, thereby obtaining 20.5 g of N-(1,1,2,2-tetrafluoro-6-hydroxy-hexane-1-sulfonyloxy)-5-norbornene-2,3-dicarboxyimide (hereinafter referred to as "a compound (13-a)") (69% yield, 98% purity).

Properties of N-(1,1,2,2-Tetrafluoro-6-Hydroxy-Hexane-1-Sulfonyloxy)-5-Norbornene-2,3-Dicarboxyimide $^1$H NMR (Solvent for measurement: Deuterated chloroform, Reference material: Tetramethylsilane) δ (ppm): 5.55 (dd, 2H), 3.50 (t, 2H), 4.58 (t, 2H), 2.94-2.75 (m, 4H), 2.49-2.51 (m, 2H), 1.80-1.53 (m, 6H).

$^{19}$F NMR (Solvent for measurement: Deuterated chloroform, Reference material: Trichlorofluoromethane) δ (ppm): −110.4 (s, 2F), −116.6 (s, 2F).

Example 6-3

Production of N-(1,1,2,2-Tetrafluoro-6-Acetoxy-Hexane-1-Sulfonyloxy)-5-Norbornene-2,3-Dicarboxyimide

[Chemical Formula 79]

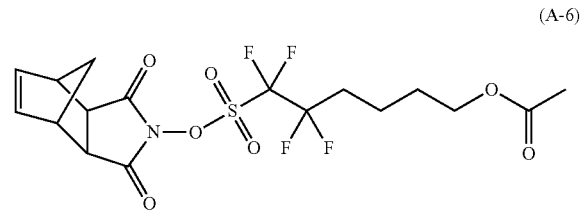

(A-6)

The same procedure as Example 1-8 was conducted with the use of 20 g (0.047 mol) of 98% purity compound (13-a) and 5 ml (0.070 mol) of acetyl chloride. As a result, there was obtained 19.7 g of N-(1,1,2,2-tetrafluoro-6-acetoxy-hexane-1-sulfonyloxy)-5-norbornene-2,3-dicarboxyimide in the form of a light brown viscous liquid (88% yield, 96% purity). This compound will be referred to as "an acid generator (A-6)".

Properties of N-(1,1,2,2-Tetrafluoro-6-Acetoxy-Hexane-1-Sulfonyloxy)-5-Norbornene-2,3-Dicarboxyimide $^1$H NMR (Solvent for measurement: Deuterated chloroform, Reference material: Tetramethylsilane) δ (ppm): 5.55 (dd, 2H), 3.50 (t, 2H), 4.58 (t, 2H), 2.94-2.75 (m, 4H), 2.49-2.51 (m, 2H), 1.97 (s, 3H), 1.80-1.53 (m, 6H).

$^{19}$F NMR (Solvent for measurement: Deuterated chloroform, Reference material: Trichlorofluoromethane) δ (ppm): −110.3 (s, 2F), −116.5 (s, 2F).

Reference Example

Evaluation Conditions

Each evaluation result of sensitivity, resolution, MEEF and LWR of radiosensitive resin compositions obtained in Reference Examples as discussed below was brought as follows.

[Sensitivity]

With regard to Reference Example, a substrate having a wafer on which surface a film of ARC29A (available from Nissan Chemical Industries, Ltd.) of 77 nm thickness is formed was used. A composition was applied to the substrate by spin coating and then subjected to SB (Soft Bake) on a hot plate for 90 seconds at a temperature as shown in Table 2, thereby forming a resist film having a film thickness of 120 nm. The resist film was subjected to exposure through a mask pattern with the use of a full field reduced projection exposure apparatus "S306C" (NA 0.78) available from NIKON CORPORATION. Thereafter, PEB (Post Exposure Bake) was conducted thereon for 90 seconds at a temperature as shown in Table 2, followed by development at 25° C. for 60 seconds with 2.38 mass % TMAH aqueous solution. Then, it was rinsed and then dried thereby forming a positive-tone resist pattern. An exposure (mJ/m$^2$) at which a line width pattern obtained in this stage through a mask of 1:1 line-and-space (1L/1S) of 90 nm dimension is formed to have a line width of 90 nm and 1L/1S will be referred to as an optimum exposure. The optimum exposure (mJ/m$^2$) will be referred to as "sensitivity".

[LWR]

In observing 90 nm-1L/1S-pattern resolved at an optimum exposure, the pattern was observed from above by using a measuring apparatus SEM S9220 available from Hitachi, Ltd. The line width pattern was observed at any 10 points at the time of observation. A value obtained by expressing the statistical dispersion with 3σ was referred to as LWR. Decrease in LWR value means increase in superiority of roughness.

[MEEF]:

With the use of a mask having a line width of 90 nm, sensitivity to the optimum exposure was measured in such a manner that the line width of 90 nm-1L/1S-pattern had a line width of 90 nm. Then, at this sensitivity, pattern dimensions resolved at mask sizes of 5 points, i.e., 85.0 nm, 87.5 nm, 90.0 nm, 92.5 nm and 95.0 nm. Results thereof were pointed with taking the mask size as the vertical axis while taking the line width as the horizontal axis, and then a gradient was obtained by the method of least squares. The gradient was referred to as MEEF.

Examples of Resin Synthesis

In 200 g of 2-butanone, 37.28 g (40 mol %) of the following compound (S-1), 18.50 g (15 mol %) of (S-2), 44.22 g (45 mol %) of (S-3) were dissolved. Additionally, 4.83 g of dimethyl 2,2'-azobis(isobutyrate) was added thereto, thereby preparing a monomer solution. A 100 0 ml three-neck flask was charged with 100 g of 2-butanone, followed by conducting 30 minutes of nitrogen purge. After conducting nitrogen purge, heating was conducted to 80° C. while stirring the reactor, followed by dropwise addition of the previously prepared monomer solution by using a dropping funnel while spending 3 hours. The initiation of dropping was put down as a polymerization initiation time, and additionally a polymerization reaction was conducted for 6 hours. After the termination of the polymerization, a polymerized solution was subjected to cooling with water, thereby being cooled to 30° C. or less. Then, the solution was made dispersed in 200 g of n-heptane to obtain a slurry, followed by rinsing. Then, an operation of separating the solution by filter was conducted 2 times, followed by drying at 50° C. for 17 hours, thereby obtaining a white powdery copolymer (a resin B-1). This copolymer was 9000 in Mw and 1.7 in Mw/Mn. As a result of $^{13}$C-NMR analysis, the copolymer was confirmed to be one having the content of each constitutional repeating unit represented by the compound (S-1), the compound (S-2) and the compound (S-3) of 45.4:11.3:43.3 (mol %). This copolymer will be referred to as a polymer (B-1).

[Chemical Formula 80]

(S-1)
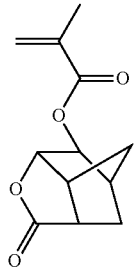

(S-2)
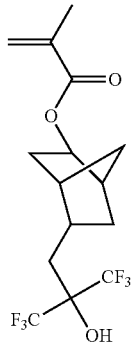

(S-3)
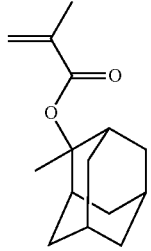

(S-4)
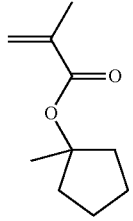

Evaluation Results 100 parts of the thus obtained polymer (B-1), 10.1 parts of the following radiosensitive acid generator (an acid generator) (A-1), 0.6 parts of the following acid diffusion inhibitor (C) were mixed, thereby obtaining a radiosensitive resin composition. As a result of conducting the above-mentioned evaluations with 100° C. of SB and 100° C. of PEB in the use of a radiosensitive resin composition solution obtained with 1880 parts of the following solvent (D-1), there were confirmed a sensitivity of 38.0 J/m², a LRW of 7.2 nm, and a MEEF of 3.0.
Radiosensitive Acid Generator (A);
[Chemical Formula 81]
(A-1)
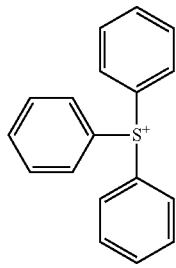
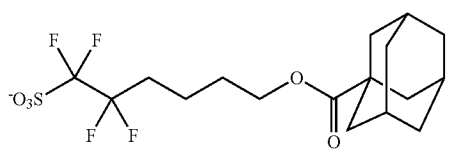
(A-2)
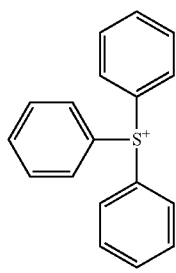
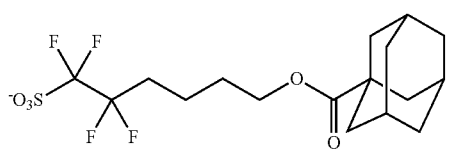
(A-3)
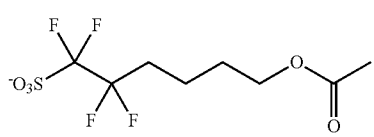
[Chemical Formula 82]
(A-4)
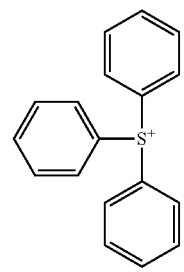
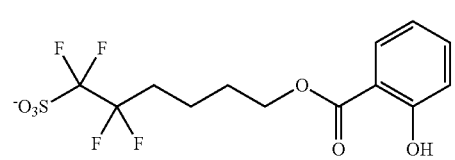
(A-5)
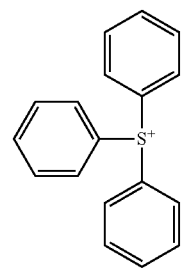
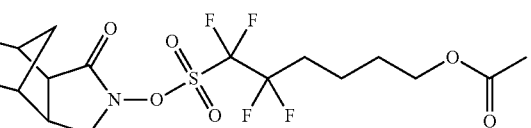
(A-6)
[Chemical Formula 83]
(A-a)
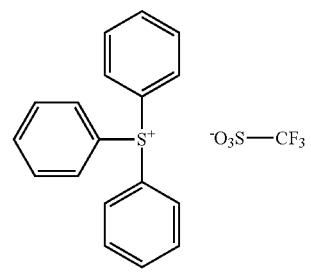

-continued

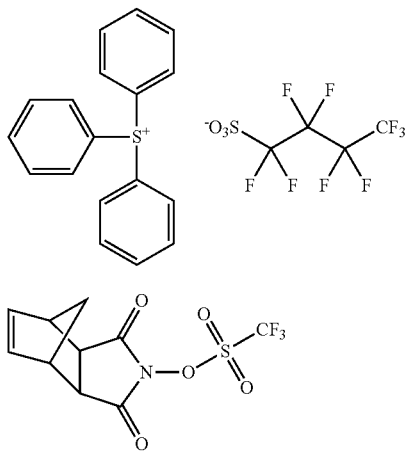
(A-b)

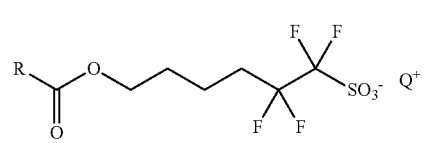

(A-c)

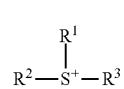

Acid Diffusion Inhibitor (C);
(C-1) Trioctylamine
Solvent (D);
(D-1); Propylene glycol monomethyl ether acetate A copolymer (a resin (B)) (B-2) was produced by employing the mole ratio as shown in the following "Copolymer (Resin (B))" as a mole ratio among the compound (S-1) and the others. A radiosensitive resin composition (Reference Examples 2 to 6 and Comparative Examples 1 to 3) was produced in the same manner as Reference Example 1 with the exception of mixing the obtained copolymer (B-2) with the above radiosensitive acid generator (A) and the above acid diffusion inhibitor (C) at a ratio as shown in Table 1.

Copolymer (Resin (B));
B-2: (S-1) 40/(S-2) 15/(S-4) 45 (charge ratio (mol %))/= 41.0112.8146.2 ($^{13}$C-NMR analysis value (mol %)), Mw=10500, Mw/Mn=1.7

TABLE 1

| | | Resin (part) | Acid Generator (part) | Acid Diffusion Inhibitor (part) | Solvent (part) |
|---|---|---|---|---|---|
| Reference Example | 1 | B-1 (100) | A-1 (10.1) | C-1 (0.6) | D-1 (1880) |
| | 2 | B-2 (100) | A-2 (10.4) | C-1 (0.6) | D-1 (1880) |
| | 3 | B-2 (100) | A-3 (8.3) | C-1 (0.6) | D-1 (1880) |
| | 4 | B-1 (100) | A-4 (9.5) | C-1 (0.6) | D-1 (1880) |
| | 5 | B-2 (100) | A-5 (8.0) | C-1 (0.6) | D-1 (1880) |
| | 6 | B-1 (100) | A-6 (9.5) | C-1 (0.6) | D-1 (1880) |
| Comparative Example | 1 | B-1 (100) | A-a (8.4) | C-1 (0.6) | D-1 (1880) |
| | 2 | B-2 (100) | A-b (6.0) | C-1 (0.6) | D-1 (1880) |
| | 3 | B-1 (100) | A-c (6.1) | C-1 (0.6) | D-1 (1880) |

TABLE 2

| | | SB (° C.) | PEB (° C.) | Sensitivity (mJ/cm$^2$) | LWR (nm) | MEEF |
|---|---|---|---|---|---|---|
| Reference Example | 1 | 100 | 115 | 38.0 | 7.2 | 3.0 |
| | 2 | 100 | 130 | 45.0 | 6.8 | 3.1 |
| | 3 | 100 | 105 | 32.0 | 6.9 | 2.8 |
| | 4 | 100 | 115 | 39.0 | 7.4 | 3.3 |
| | 5 | 90 | 130 | 57.0 | 7.2 | 3.2 |
| | 6 | 100 | 105 | 38.0 | 7.1 | 2.9 |
| Comparative Example | 1 | 100 | 115 | 36.0 | 8.2 | 3.8 |
| | 2 | 90 | 130 | 55.0 | 9.0 | 4.6 |
| | 3 | 100 | 105 | 20.0 | 7.2 | 6.6 |

The invention claimed is:

1. A sulfonic acid onium salt compound represented by the following general formula (2)

$$\text{(2)}$$

[Structure: R-C(=O)-O-(CH$_2$)$_3$-C(F)(F)-C(CF$_3$)(-)-SO$_3^-$ Q$^+$ — structural formula (2)]

wherein R represents
(a) a linear or branched monovalent hydrocarbon group selected from methyl group, ethyl group, n-propyl group, i-propyl group, n-butyl group, t-butyl group, n-pentyl group, i-pentyl group, n-hexyl group, i-hexyl group, n-heptyl group, n-octyl group, i-octyl group, n-nonyl group, n-decyl group, 2-ethylhexyl group and n-dodecyl group,
(b) a monovalent hydrocarbon group having a cyclic or a partially cyclic structure selected from cyclopropyl group, cyclobutyl group, cyclopentyl group, cyclohexyl group, bornyl group, norbornyl group, adamantyl group, pinanyl group, thujyl group, caryl group, camphanyl group, cyclopropylmethyl group, cyclobutylmethyl group, cyclopentylmethyl group, cyclohexylmethyl group, bornylmethyl group, norbornylmethyl group and adamantylmethyl group,
(c) an aryl group selected from phenyl group, 1-naphthyl group, 2-naphthyl group, 1-anthryl group, 1-phenanthryl group, or
(d) a heterocyclic organic group selected from furyl group, thienyl group, piranyl group, pyrrolyl group, thianthrenyl group, pyrazolyl group, isothiazolyl group, isoxazolyl group, pyrazinyl group, pyrimidinyl group, pyradazinyl group and monocyclic or polycyclic lactone,
wherein any of the group selection from (a) to (d) may have a substituent selected from fluorine, chlorine, bromine, iodine, hydroxyl group and thiol group,
wherein any of the group selection from (a), (b) and (d) may have an aryl group as a substituent or have a keto group in which two hydrogen atoms on the same carbon in the hydrocarbon group are substituted with one oxygen atom,
wherein the group selected form (c) may have an alkyl group as a substituent, and
wherein Q$^+$ represents a monovalent onium cation.

2. A sulfonic acid onium salt compound as claimed in claim 1, wherein Q$^+$ is a sulfonium cation represented by the following general formula (i)

$$\text{(i)}$$

$$R^2 - \overset{R^1}{\underset{}{S^+}} - R^3$$

wherein R$^1$, R$^2$ and R$^3$ mutually independently represent a substituted or unsubstituted linear or branched alkyl group having 1 to 10 carbon atoms or a substituted or unsubstituted aryl group having 6 to 18 carbon atoms, and alternatively, any two or more of R$^1$, R$^2$ and R$^3$ bond mutually to form a ring together with sulfur atom as shown in the formula.

3. A sulfonic acid onium salt compound as claimed in claim 1, wherein $Q^+$ is an iodonium cation represented by the following general formula (ii)

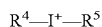 (ii)

wherein $R^4$ and $R^5$ mutually independently represent a substituted or unsubstituted linear or branched alkyl group having 1 to 10 carbon atoms or a substituted or unsubstituted aryl group having 6 to 18 carbon atoms, and alternatively, $R^4$ and $R^5$ are bonded mutually to form a ring together with iodine atom as shown in the formula.

4. A N-sulfonyloxyimide compound represented by the following general formula (3)

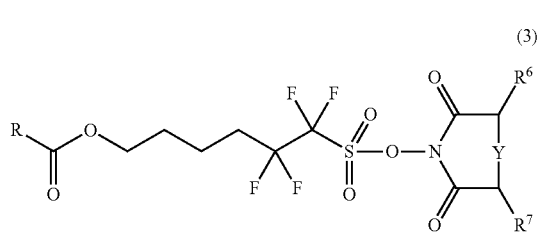

(3)

wherein R has the same meaning as that in claim 1, wherein $R^6$ and $R^7$ mutually independently represent hydrogen atom or a substituted or unsubstituted monovalent organic group, and alternatively, $R^6$ and $R^7$ form a ring together with the carbon atoms to which they bond mutually, and wherein Y represents a single bond, a double bond or a divalent organic group.

5. A sulfonic acid salt represented by the following general formula (4)

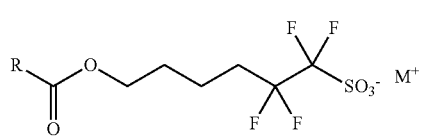

(4)

wherein R has the same meaning as that in claim 1, and
wherein M represents Na, K or Li.

6. A sulfonic acid represented by the following general formula (5)

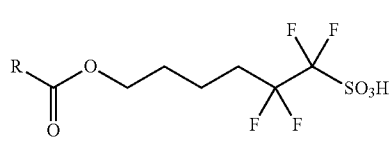

(5)

wherein R has the same meaning as that in claim 1.

7. A radiosensitive acid generator for a chemically amplified resist material, wherein the radiosensitive acid generator is sensitive to high energy rays comprising ultraviolet rays, far ultraviolet rays, extreme ultraviolet rays (EUV), electron beam, X-rays, excimer laser, γ-rays or synchrotron radiation irradiation, thereby generating a sulfonic acid as claimed in claim 6.

8. A radiosensitive acid generator for a chemically amplified resist material, comprising:
ic acid onium salt compound as claimed in claim 1,
wherein the radiosensitive acid generator is sensitive to high energy rays comprising ultraviolet rays, far ultraviolet rays, extreme ultraviolet rays (EUV), electron beam, X-rays, excimer laser, γ-rays or synchrotron radiation irradiation.

9. Triphenylsulfonium 1,1,2,2-tetrafluoro-6-(1-adamantanecarbonyloxy)-hexane-1-sulfonate.

10. A process for producing a sulfonic acid onium salt compound represented by the following general formula (2),

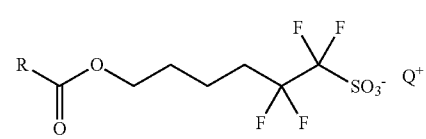

(2)

comprising the steps of:
a $1^{st}$ step of sulfinating 6-bromo-5,5,6,6-tetrafluorohexan-1-ol by using a sulfinating agent thereby obtaining a sulfinic acid salt represented by the following general formula (7);

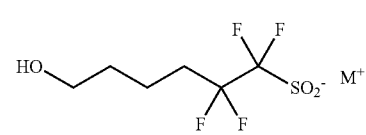

(7)

a $2^{nd}$ step of oxidizing the sulfinic acid salt obtained by the $1^{st}$ step and represented by the general formula (7) by using an oxidizing agent, thereby obtaining a sulfonic acid salt represented by the following general formula (4);

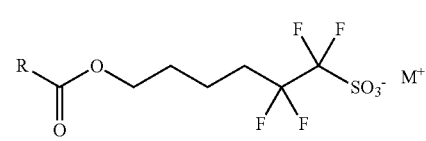

(4)

a $3^{rd}$ step of reacting the sulfonic acid salt obtained by the $2^{nd}$ step and represented by the general formula (4) with a monovalent onium salt represented by the following general formula (8)

 (8)

thereby obtaining a sulfonic acid onium salt represented by the following general formula (9); and

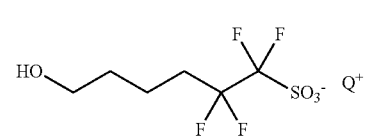

(9)

a $4^{th}$ step of reacting the sulfonic acid onium salt obtained by the $3^{rd}$ step and represented by the general formula (9) with acid or acid halide represented by the following general formula (10)

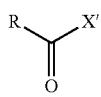

or with acid anhydride represented by the following general formula (11)

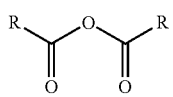

thereby obtaining a sulfonic acid onium salt compound represented by the general formula (2), wherein R has the same meaning as that in claim 1,
wherein $Q^+$ represents a monovalent onium cation,
wherein M represents Na, K or Li,
wherein $X^-$ represents a monovalent anion, and
wherein X' represents hydroxyl group, fluorine atom, chlorine atom, bromine atom or iodine atom.

11. A radiosensitive acid generator for a chemically amplified resist material, comprising:

a N-sulfonyloxyimide compound as claimed in claim 4,
wherein the radiosensitive acid generator is sensitive to high energy rays comprising ultraviolet rays, far ultraviolet rays, extreme ultraviolet rays (EUV), electron beam, X-rays, excimer laser, γ-rays or synchrotron radiation irradiation.

12. A compound represented by any of the formulas (A-1) to (A-6)

(A-1)
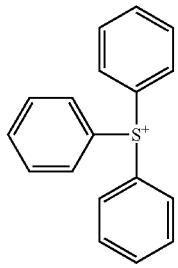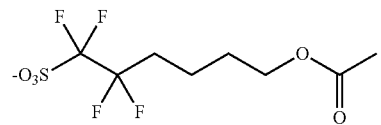

(A-2)
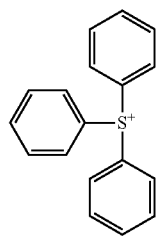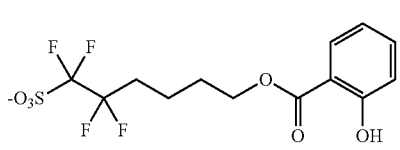

(A-3)
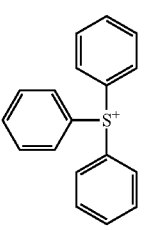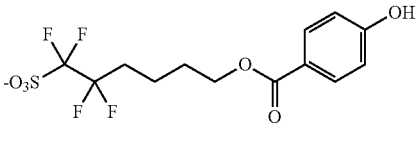

(A-4)
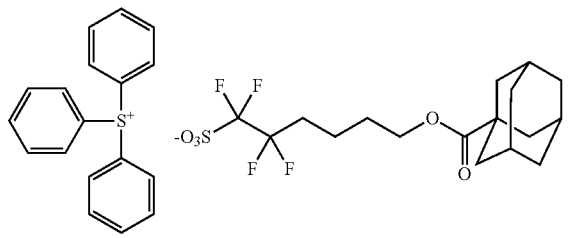

(A-5)
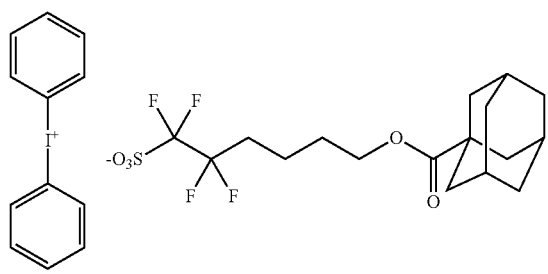

(A-6)
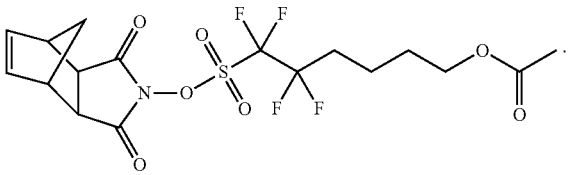

13. A radiosensitive acid generator for a chemically amplified resist material, comprising:

any of the compound as claimed in claim 12,
wherein the radiosensitive acid generator is sensitive to high energy rays comprising ultraviolet rays, far ultraviolet rays, extreme ultraviolet rays (EUV), electron beam, X-rays, excimer laser, γ-rays and synchrotron radiation irradiation.

14. A radiosensitive acid generator for a chemically amplified resist material, comprising:

a compound as claimed in claim 9,
wherein the radiosensitive acid generator is sensitive to high energy rays comprising ultraviolet rays, far ultraviolet rays, extreme ultraviolet rays (EUV), electron beam, X-rays, excimer laser, γ-rays or synchrotron radiation irradiation.

* * * * *